United States Patent
Inpanbutr

(10) Patent No.: US 7,129,230 B2
(45) Date of Patent: Oct. 31, 2006

(54) METHOD AND PRODUCT FOR TREATING CANCER IN PETS

(75) Inventor: Nongnuch Inpanbutr, Upper Arlington, OH (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/804,111

(22) Filed: Mar. 12, 2001

(65) Prior Publication Data

US 2002/0127267 A1   Sep. 12, 2002

(51) Int. Cl.
*A61K 31/59* (2006.01)
*A61K 47/00* (2006.01)

(52) U.S. Cl. ..................... 514/167; 424/439
(58) Field of Classification Search ............... 514/167; 424/439
See application file for complete search history.

(56) References Cited

U.S. PATENT DOCUMENTS

| | | | |
|---|---|---|---|
| 4,022,891 A | 5/1977 | Takeshita et al. |
| 4,341,774 A | 7/1982 | Aoki et al. |
| 4,364,941 A | 12/1982 | Kiyoki et al. |
| 4,442,093 A | 4/1984 | Maeda et al. |
| 4,948,789 A | 8/1990 | Slatopolsky |
| 5,043,170 A | 8/1991 | Borenstein et al. |
| 5,063,221 A | 11/1991 | Nishii et al. |
| 5,087,619 A * | 2/1992 | Baggiolini et al. |
| 5,145,846 A | 9/1992 | Baggiolini et al. |
| 5,183,815 A | 2/1993 | Saari et al. |
| 5,250,523 A | 10/1993 | DeLuca et al. |
| 5,597,815 A | 1/1997 | Deluca et al. |
| 5,602,116 A | 2/1997 | Knutson et al. |
| 5,707,980 A | 1/1998 | Knutson et al. |
| 5,861,386 A | 1/1999 | Knutson et al. |
| 5,869,473 A | 2/1999 | Knutson et al. |
| 5,972,917 A | 10/1999 | Bishop et al. |

OTHER PUBLICATIONS

Yu et al., Vitamin D analogs: new therapeutic agents for the treatment of squamous cancer and its associated hypercalcemia, abstract, PMID: 7756673, Feb. 1995.*
Katzung, Basic and Clinical Pharmocology, 1995, pp. 661-663, 838, 841, 830-832, 537-538.*
Hardman et al., Goodman and Gilman's The pharmacological Basis of Therapeutics, ninth edition1996, p. 539.*
Bouillon et al., Endocrine Reviews, 995; 16(2):200-257.*
Abdaimi et al., Cancer Research, 1999; 59:3325-3328.*
Yu, J.; Papavasiliou, V; Rhim, J; Goltzman, D; Kremer, R: "Vitamin D Analogs: New Therapeutic Agents For The Treatment Of Squamous Cancer And Its Associated Hypercalcemia," *Anticancer Drugs* Feb. 1995;6(1):101-8, abstract only.
Werkmeister, Jr; Merryman, Ji; McCauley, L; Horton, JE; Capen, CC; Rosol, TJ; "Parathyroid Hormone-related Protein Production By Normal Human Keratinocytes In Vitro," *Exp Cell Res* Sep. 1993;208(1):68-74, abstract only.
Merryman, JI; Capen, CC; McCauley, LK; Werkmeister, Jr; Suter, MM; Rosol, TJ: "Regulation Of Parathyroid Hormone-related Protein Production By A Squamous Carcinoma Cell Line In Vitro," *Lab Invest* Sep. 1993;69(3):347-54, abstract only.

(Continued)

*Primary Examiner*—San-Ming Hui
(74) *Attorney, Agent, or Firm*—Bell, Boyd & Lloyd LLC

(57) ABSTRACT

A pet food containing vitamin D analogs for use in treatment of cancer in pets, such as dogs and cats, is described. Also described is a method for treating pets, such as dogs and cats, for cancer by feeding the pet a pet food containing at least one vitamin D analog.

31 Claims, 11 Drawing Sheets vitamin $D_3$ $1\alpha,25\text{-}(OH)_2\text{-}D_3$ $1\alpha,25\text{-}(OH)_2\text{-}16\text{-ene-}23\text{-yne-}D_3$ (analog V)

$1\alpha,25$–dihydroxy-22,24-diene-24,26,27-trihomovitamin D (EB1089)

OTHER PUBLICATIONS

Wang, X; Chen, X.; Akhter, J; Morris, DL: "The *In Vitro* Effect Of Vitamin D3 Analogue EB-1089 On A Human prostate Cancer Cell Line (PC-3)," *British Journal Of Urology* (1997), 80, 260-262.

Colston, KW; James, SY; Ofori-Kuragu, EA; Binderup, L; Grant, AG: "Vitamin D Receptors And Anti-proliferative Effects Of Vitamin D Derivatives In Human Pancreatic Carcinoma Cells In Vivo And In Vitro," *British Journal of Cancer*(1997)76(8), 1017-1020.

Berg, Jens P.; Liane, Kjellaug, M.; Bjørhovde, Siri B.; Bjøro, Trine; Torjesen, Peter A.; Haug, Egil: Vitamin D Receptor Binding And Biological Effects Of Cholecalciferol Analogues In Rat Thyroid Cells,: *J. Steroid Biochem.Molec.Biol.* vol. 50.

Skowronski, Roman J.; Peehl, Donna M.; Feldman, David: "Actions Of Vitamin $D_3$ Analogs On Human Prostate Cancer Cell Lines: Comparison With 1,25-Dihydroxyvitamin $D_3$," *Encocrinology* 1995 by The Endocrine Society.

Koli, Katri; Keski-Oja, Jorma: "1,25-Dihydroxyvitamin $D_3$ Enhances The Expression Of Transforming Growth Factor B1 And Its Latent Form Binding Protein In cultured Breast Carcinoma Cells," *Cancer Research* 55, 1540-1546, Apr. 1, 1995.

Moore, Theodore B.; Koeffler, H. Phillip; Yamashiro, Joyce M.; Wada, Randal K.: "Vitamin $D_3$ Analogs Inhibit Growth And Induce differentiation In LA-N-5 Human Neuroblastoma Cells," *Clin.Exp. Metastasis*, 1996, 14, 239-245.

Zhou, Jian-Yuan; Norman, Anthony W.; Chen, Dan-Lin; Sun, Guo-Wen; Uskokovic, Milan: "1-25-Dihydroxy-16-ene-23-yne-vitamin $D_3$ Prolongs Survival Time Of Leukemic Mice," *Proc. Natl. Acad. Sci. USA*, vol. 87, pp. 3939-3932 May 1990 Medical Sciences.

Zhou, Jian-Yuan; Norman, A.W.; Lubvert, M.; Collins, E.D.; Uskokovic, M.R.; Koeffler, H.P.: "Novel Vitamin D Analogs That Modulate Leukemic Cell Growth And Differentiation With Little Effect On Either Intestinal Calcium Absorption Or Bone Calcium Mobilization," *Blood*, vol. 74, No. 1Jul. 1989: pp. 82-93.

Norman, Anthony W.; Zhou, J.Y.; Henry, Helen L.; Uskokovic, Milan R.; Koeffler, H. Phillip: "Structure-Function Studies On Analogues Of 1α, 25-Dihydroxyvitamin $D_3$: Differential Effects on Leukemic Cell Growth, Differentiation, and Intestinal Calcium Absorption," *Cancer Research* 50,6857-6864, Nov. 1, 1990.

Norman, AW; Sergeev, IN; Bishop, JE; Okamura, WH: "Selective Biological Response By Target Organs (intestine, kidney, and bone) to 1,25-dihydroxyvitamin $D_3$:and Two Analogues," *Cancer Res* (United States), Sep. 1, 1993, 53 (17) p. 3935-42, abstract only.

Shams, G; Romstedt, KJ; Gerhardt, MA; Harrold, MW; Miller, DD; Feller, DR: "Pharmacological Evaluation of the Beta-adrenoceptor Agonist and Thromboxane Receptor Blocking Properties of 1-benzyl Substituted Trimetoquinol Analogues," *J Pharmacol* (Netherlands), Aug. 2, 1990, 184 (1) p. 21-31, abstract only.

Pressova, M; Smrt, J: "Lipid Derivatives of (2'-5') Oligo A," *Nucleic Acids Symp Ser* (England), 1987, (18) p. 101-4, abstract only.

Tse, FL; Christiano, Jr; Talbot, KC: "Relative Absorption of Trytophan Ethyl Ester Amide Derivatives With Various Fatty Acid Chains In The Dog," *J Pharm Pharmacol* (England), Sep. 1984, 36(9) p. 633-6, abstract only.

Bikolics, K; Bieglmayer, C; Spona, J; Serprodi, J; Teplan, I: "Inhibition of LH-release By Synthetic Analogues of LH-RH in Rat Pituitary Cell Culture," *Peptides* (United States), Spring 1981, 2(1) p. 65-73, abstract only.

Gudkov, ND; Stolovitskii, Ium; Evstigneev, VB: "Impulse Photoconductivity of Solutions of Chlorophyll and its Analogs," *Biofizika* (USSR), Mar.-Apr. 1975, 20(2) p. 214-8, abstact only.

Lan, SJ; Dean, AV; Walker, BD; Schreiber, EC: "Metabolism of a Benzothiazine Compound by the Intact Rat, Isolated Perfused Rat Liver, and Rat-liver Microsomes," *Xenobiotica* (England), Mar. 1976,6(3) p. 171-83, abstract only.

Poirer, MA; Black, DB; Lovering, EG: "Formation of Alkyl Carbamates From Glyburide: Potential for Overestimation in the BP Glibenclamide (Glyburide) Foreign Substances Test," *Can. J. Pharm. Sci.*; vol. 15 ISS, Jan. 1980, p. 8-9, abstract only.

Bowman, JC; Beroza, M; Harding, JA: "Determination of Phorate and Five of Its Metabolites in Corn," *J. Agr. Food Chem.*; 17(1), 138-42, 1969, abstract only.

Uchiyama, Minoru; Murakami, Toshiki: "Effects of AVT and Vascular Antagonists on Kidney function and Smooth Muscle Contraction in the River Lamprey, Lampetra Japonica," *Comparative Biochemistry and Physiology A Comparative Physiology*, 107 (3):p. 493-499 1994, abstract only.

Manhi, FM; Abdel-Fattah, AM: "Reactions with 6-substituted-2-thiouracil-5-carbonitriles. Synthesis of Tetrazolo (1,5-c) and Ditetrazolo (1, 5-a: 1, 5-c) Pyrimidines," *Egyptian Journal of Pharmaceutical Sciences*, 33 (5-6):p. 825-838, 1992 (1993), abstract only.

Compton, DR; Johnson, MR; Melvin, LS; Martin, BR: "Pharmacological Profile of a Series of Bicyclic Cannabinoid Analogs Classification as Cannabimimetic Agents," *J Pharmacol Exp Ther* 260 (1). 1992. 201-209, abstract only.

Ahmad, MS; Husain, SR; Husain M.; Choudhry, ZH: "On The synthesis of Some More Steroidal Tetrazoles," *Indian J Chem Sect B Org Chem Incl Med Chem* 16 (7). 1978 559-562, abstract only.

Chu, CK; Reichman, U; Watanabe, KA; Fox, JJ: "Nucleosides Part 109 2 Deoxy-PSI ISO Cytidine 2 Deoxy-PSI Uridine and 2 Deoxy-1-Methyl-PSI Uridine Isosteres of Deoxy Cytidine Deoxy Uridine and Thymidine," *J Heterocyclic Chemistry*, 14 (6). 1977 1119-1121, abstract only.

Chinn, MK; Myburgh, KH; Pham, T; Franksskiba, K; Cooke, R.: "The Effect of Polyethylene Glycol on the Mechanics and ATPase Activity of Active Muscle Fibers," *Biophysical Journal*, 2000, V78, N2 (Feb.), p. 927-939, abstract only.

Kumar, V; Coulsell, E; Ober, B; Hubbard, G; Sercarz, E; Ward, ES: "Recombinant T Cell Recpetor Molecules Can Prevent And Reverse Experimental Autoimmune Encephalomyelitis—Dose Effects and Involvement of Both CD4 and CD8 T Cells," *Journal Of Immunology*, 1997, V159, N10 (Nov. 15), p. 5150-5156, abstract only.

Lefloch, C; Henderson, RA; Hitchcock, PB; Hughes, DL; Janas, Z; Richards, RL; Sobata, P; Szafert, S: "Reactions of Substituted Hydrazines With Vandium(iii) Compounds—Crystal-Structures of [NH(2)ME(2)](2)[(VCL3)(2)(MU-NNME(2)) (3)], [V(0C6H3PR2I-2,6)(3) (NH(2)NME(2)) (2)], AND [V(0C6H3PR2I-2,6) (3) (NH(2)NMEPH)2]," *Journal of the Chemical Society-Dalton Transactions*, 1996, N13 (Jul. 7), p. 2755-2762, abstract only.

Bhaumik, A; Dongare MK; Kumar, R: "Synthesis of MTW-Type Microporous Material and Its Vanadium-Silicate Analog Using a New Diquatemary Ammonium Cation as a Template," *Microporous Materials*, 1995, V5, N3 (Nov.), p. 173-178, abstract only.

Rehder, D: "Structure and Function of Vanadium Compounds in Living Organisms," *Biometals*, 1992, V5, N1 (SPR), P3-12.

Kabanos, TA; White, AJP; Williams, DJ; Woollins, JD: "Synthesis and X-ray Structures of BIS (3, 5-Di-Tert-Butycatecholato) (Phenanthroline) Vanadium (IV) and its Vanadium(V) Analog [V(DTBC) 2 (PHEN)][SBF6]," *Journal of the Chemical Society-Chemical Communications*, 1992, N1 (Jan. 1), p. 17-18.

Toverud, SU; Anderson, JJB; Garner, SC: "Vitamin D," *Food Science & Technology*, 1995.

Norman, AW; Sergeev, IN; Bishop, JE; Okamura, WH: "Selective Biological Response by Target Organs (intestine, kidney, and bone) to 1,25-dihydroxyvitamin Dinf 3 and Two Analogues," *Cancer Research*, (United States) 1993, 53/17 (3935-3942).

Van Den Bemd, G-JCM; Pols, HAP; Birkenhager, JC; Kleinekoort, WMC; Van Leeuwen, JPTM: *IMSWorld R&D Focus*, Jun. 28, 1999.

El Abdamimi, K; Papavasiliou, V; Rabbani, SA; Rhim, JS; Goltzman, D; Dremer, R: "Reversal of Hypercalcemia with the Vitamin D Analogue EB1089 In A Human Model of Squamous Cancer," *Cancer Research*, (United States), Jul. 15, 1999, 59 (14) p. 3325-8.

Koszewski, JN; Reinhardt, TA; Horst, RL: "Differential Effects of 20-3pi Vitamin D Analogs on the Vitamin D Receptor Homodimer," *J Bone Miner Res* (United States) Apr. 1999, 14 (4) p. 509-17.

Koshizuka, K; Koike, M; Asou, H; Cho, SK; Stephen, T; Rude, RK; Binderup, L; Uskokovic, M; Koeffler, HP: "Combined Effect of Vitamin $D_3$Analogs and Paclitaxel on the Growth of MCF-7 Breast Cancer Cells In Vivo," *Breast Cancer Res Treat* (Netherlands), Jan. 1999, 53 (2) p. 113-20.

Koshizuke, K; Kubota, T; Said, J; Koike, M; Binderup, L; Uskokovic, M; Koeffler, HP: "Combination Therapy of a Vitamin D$_3$ Analog and All-Trans-Retinoic Acid: Effect on Human Breast Cancer in Nude Mice" *Anticancer Res* (Greece), Jan.-Feb. 1999, 19 (1A) p. 519-24.

Lokeshwar, BL; Schwartz, GG; Selzer, MG; Burnstein, KL; Zhuang, SH; Block, NL; Binderup, L: "Inhibition of Prostate Cancer Metastasis in vivo: a comparison of 1,23-dihydroxyvitamin D (calcitriol) and EB1089," *Cancer Epidemiol Biomarkers Prev* (United States), Mar. 1999, 8(3) p. 241-8.

Nickerson, T; Huynh, H: "Vitamin D Analogue EB1089-Induced Prostate Regression is Associated With Increased Gene Expression of Insulin-like Growth Factor Binding Proteins," *J Endocrinol* (England), Feb. 1999, 160(2) p. 223-9.

James, SY; Mercer, E; Brady, M; Binderup, L; Colston, KW: "A Synthetic Analogue of Vitamin D, Induces Apoptosis in Breast Cancer Cells In Vivo and In Vitro," *Br J Pharmacol* (England), Nov. 1998, 125 (5) p. 953-62.

Mathiasen, IS; Colston, KW; Binderup, L: "A Novel Vitamin D Analogue, Has Strong Antiproliferative and Differentiation Inducing Effects On Cancer Cells," *J Steroid Biochem Mol Biol* (England), Sep. 1993, 46(3) p. 365-71.

Somjan, D.; Waisman, A; Weisman, J; Kaye, Am: "Nonhypercalcemic Analogs of Vitamin D Stimulate Creatine Kinase B Activity in Osteoblast-like ROS 17/2.8 Cells and Up-regulate Their Responsiveness to Estrogens," *Steroids* (United States) May-Jun. 1998, 63 (5-6) p. 340-3.

Vanweelden, K.; Flanagan, L; Binderup, L; Tenniswood, M; Welsh, J: "Apoptotic Regression of MCF-7 Xenografts in Nude Mice Treated with the Vitamin D$_3$ Analog," *Endocrinology* (United States) Apr. 1998, 139(4)—2102-10.

Hansen, CM; Maenpaa, PH: "A Novel Vitamin D Analog With Strong Antiproliferative and Differentiation-inducing Effects on Target Cells," *Biochem Pharmacol* (England), Dec. 1, 1997, 54(11) p. 1173-9.

Danielsson, C; Mathiasen, IS; James, SY; Nayeri, S; Bretting, C; Hansen, CM; Colston, KW; Carlberg, C: "Sensitive Induction of Apoptosis in Breast Cancer Cells by a Novel 1,25-dihydroxyvitamin D$_3$," *J Cell Biochem* (United States), Sep. 15, 1997, 66(4) p. 552-62.

Colston, KW; James, SY; Ofori-Kuragu, EA; Binderup, L; Grant, AG: "Vitamin D Receptors and Anti-proliferative Effects of Vitamin D Derivatives in Human pancreatic Carcinoma Cells In Vivo and In Vitro," *Br J Cancer* (Scotland) 1997, 76(8) p. 1017-20.

Schrader, M; Kahlen, JP; Carlberg, C: "Functional Characterization of a Novel Type of 1 Alpha, 25-dihydroxyvitamin D$_3$ Response Element Identified in the Mouse C-fos Promoter," *Biochem Biophys Res Commun* (United States) Jan. 23, 1997, 230(3) p. 646-51.

Zugmaier, G; Jager, R; Grage, B; Gottardis, MM; Havemann, K; Knabble, C: "Growth-inhibitory Effects of Vitamin D Analogues and Retinoids on Human Pancreatic Cencer Cells," *Br J Cancer* (Scotland), Jun. 1996, 73 (11) p. 1341-6.

Kissmeyer, AM; Binderup, E; Binderup, L; Mork, Hansen C; Andersen, NR; Makin, HL; Schroeder, NJ; Shankar, VN; Jones, G: "Metabolism of the Vitamin D Analog EB 1089: Identification of In Vivo and In Vitro Liver Metabolites and Their Biological Activities," *Biochem Pharmacol* (England) Apr. 25, 1997, 53 (8) p. 1087-97.

Pakkala, I; Savli, H; Knuutila, S; Binderup, L; Pakkala, S: "CB1093, a Novel Vitamin D Analog; Effect on Differentiation and Clonal Growth on HL-60 and de novo Leukemia Cells," *Leuk Res* (england) Apr. 1997, 21 (4) p. 321-6.

de Vos, S; Holden, S; Heber, D; Elstner, E; Binderup, L; Uskokovic, M; Rude, B; Chen, DL; Le, J; Cho, SK; Koeffler, HP: "Effects of Potent Vitamin D$_3$ Analogs on Clonal Proliferation of Human Prostate Cancer Cell Lines," *Prostate* (United States), May 1, 1997, 31 (2) p. 77-83.

Akhter, J; Chen, X; Bowrey, P; Bolton, EJ; Morris, DL: "Vitamin D$_3$ Analog, EB1089, Inhibits Growth of subcutaneous Xenografts of the Human Colon Cancer Cell Line, LoVo, in a Nude Mouse Model," *Dis Colon Rectum* (United States) Mar. 1997, 40 (3) p. 317-21.

Lamari, Y; Garel, JM: "Decrease in CGRP and CT Levels Either contained in or Released by CA-77 C Cells After Combined Treatments with 1,25-dihydroxyvitamin D$_3$ Analogues and 9-cis Retinoic Acid," *Reprod Nutr Dev* (France) 1997, 37 (1) p. 3-12.

Musiol, Im; Feldman, D: "1,25-dihydroxyvitamin D$_3$ Induction of Nerve Growth Factor in L929 Mouse Fibroblasts: Effect of Vitamin D Receptor Regulation and Potency of Vitamin D$_3$ Analogs," *Endocrinology* (United States), Jan. 1997, 138 (1)—12-8.

James, SY; MacKay, AG; Colston, KW: "Effects of 1,25 Dihydroxyvitamin D$_3$ and Its Analogues on Induction of Apoptosis in Breast Cancer Cells," *J Steroid Biochem Mol Biol* (England), Jul. 1996, 58 (4) p. 395-401.

Baudet, C; Chevalier, G; Naveilhan, P; Binderup, L; Brachet, P; Wion, D: "Cytotoxic Effects of 1 Alpha, 25-dihydroxyvitamin D$_3$ and Synthetic Vitamin D$_3$ Analogues on a Glioma Cell Line," *Cancer Lett* (Ireland), Feb. 27, 1996, 100 (1-2) p. 3-10.

Roy, S; Martel, J; Tenenhouse, HS: "Comparative Effects of 1,25-dihydroxyvitamin D$_3$-24-hydroxylase," *J Bone Minder Res* (United States) Dec. 1995, 10 (12) p. 1951-9.

Wiberg, K; Ljunghall, S; Binderup, L; Ljunggren, O: "Studies on Two New Vitamin D Analogs, EB 1089 and KH 1060: Effects on Bone Resorption and Osteoclast Recruitment In Vitro," *Bone* (United States) Oct. 1995, 17 (4) p. 391-5.

van den Bemd, GJ; Pols, HA; Birkenhager, JC; Kleinekoort, WM; van Leeuwen, JP: "Differential Effects of 1,25-dihydroxyvitamin D$_3$-Analogs on Osteoblast-like Cells and on In Vitro Bone Resorpiton," *J Steroid Biochem Mol Biol* (England), Dec. 1995, 55 (3-4) p. 337-46.

Davicco, MJ; Coxam, V; Gaumet, N; Lebecque, P; Barlet, JP: "EB 1089, a Calcitriol Analogue, Decreases Fetal Calcium Content When Injected into Pregnant Rats," *Exp Physiol* (England), May 1995, 80 (3) p. 449-56.

Okamura, WH; Midland, MM; Norman, AW; Hammond, MW; Dormanen, MC; Nemere, I: "Biochemical Significance of the 6-s-cis Conformation of the Steroid Hormone 1 Alpha, 25-dihydroxyvitamin D$_3$ Based on the Provitamin D Skeleton," *Ann N Y Acad Sci* (United States) Jun. 12, 1995, 761 p. 344-8.

Yu, J; Papavasiliou, V; Rhim, J; Goltzman, D; Kremer, R: Vitamin d Analogs: "New Therapeutic Agents for the Treatment of Squamous Cancer and its Associated Hypercalcemia," *Anticancer Drugs* (england), Feb. 1995, 6 (1) p. 101-8.

Vink-Van Wijngaarden, T; Birkenhager, JC; Kleinekoort, WM; van den Bemd, GH; Pols, HA; van Leeuwen, JP: "Antiestrogens Inhibit in Vitro Bone Resorption Stimulated by 1,25-dihydroxyvitamin D$_3$ and the vitamin D$_3$ Analogs," *Endocrinology* (United States) Feb. 1995, 136 (2) p. 812-5.

Berg, JP; Liane, KM; Bjorhovde, SB; Bjoro, T; Torjesen, PA; Haug, E: "Vitamin D Receptor Binding and Biological Effects of Cholecalciferol Analogues in Rat Thyroid Cells," *J Steroid Biochem Mol Biol* (England) Aug. 1994, 50 (3-4) p. 145-50.

Carlberg, C; Mathiasen, IS; Saurat, JH; Binderup, L: "The 1,25-dihydroxyvitamin D$_3$ (VD) Analogues MC903, EB1089 and KH1060 Activate the VD Receptor: Homodimers Show Higher Ligand Sensitivity Than Heterodimers with Retinoid X Receptors," *J Steroid Biochem Mol biol* (England), Nov. 1994, 51 (3-4) p. 137-42.

Haq, M; Kremer, R; Goltzman, D; Rabbani, SA: "A Vitamin D Analogue (EB1089) Inhibits Parathyroid Hormone-related Peptide Production and Prevents the Development of Malignancy-Associated Hypercalcemia In Vivo," *J Clin Invest* (United States) Jun. 1993, 91 (6) p. 2416-22.

Colston, KW; MacKay, AG; James, SY; Binderup, L; Chander, S; Coombes, RC: "A New Vitamin D Analogue that Inhibits the Growth of Breast Cancer Cells In Vivo and In Vitro," *Biochem Pharmacol* (England), Dec. 15, 1992, 44 (12) p. 2273-80.

Lee, Young Yiul; Park, Woo Hyun; Seol, Jae Goo; Kim Eun, Shil; Hyun, Jung Mi; Seol, Jae Goo; Kim, Eun Shil; Hyun, Jung Mi; Jung, Chul Won; Lee, Chung Choo; Kim, Byoung Kook: "Cell Cycle Arrest Induced by Vitamin D$_3$ Analog, EB1089, in NCI-H929 Myeloma Cells is Associated with Induction of Cyclin-dependent Kinase Inhibitor, p. 27," *Blood* 94 (10 Suppl. 1 Part 2): p. 158b Nov. 15, 1999.

Lee, Young Yiul; Park, Woo Hyun; Seol, Jae Goo; Kim, Eun Shil; Hyun, Jung Mi; Jung, Chul Won; Lee, Chung Choo; Kim, Byoung Kook: "Induction of Apoptosis by Vitamin D$_3$ Analog, EB1089, in NCI-H929 Myeloma Cells Via Activation of Caspase-3 and p38 Map Kinase," *Blood* 94 (10 Suppl. 1 Part 2): p. 158b Nov. 15, 1999.

Xie, SP; Pirianov, G; Coston, KW: "Vitamin D Analogues Suppress IGF-I signalling and Promote Apoptosis in Breast Cancer Cells," *European Journal of Cancer*, 35 (12):p. 1717-1723 Nov. 1999.

Stenfeldt, Mathiasen Ida; Lademann, Ulrik; Jaattela, Marja: "Apoptosis Induced by Vitamin D Compounds in Breast Cancer Cells is Inhibited by Bcl-2 But does Not Involve Known Caspases or p53," *Cancer Research* 59 (19):p. 4848-4856 Oct. 1, 1999.

Lin, R; Akutsu, N; Bastien, Y; Henderson, JE; White, JH: "Regulation of Vascular Endothelial Growth Factor Gene Expression by Vitamin $D_3$," *Journal of Bone and Mineral Research*, 14 (SUPPL. 1):p. S424 Sep. 1999.

Narayanan, R; Smith, CL; Weigel, NL: "EB1089 Treatment Partially Reverses the Reduction in vitamin D Receptor Activity in MG-63 Cells Subjected to Simulated Microgravity," *Journal of bone and Mineral Research* 14 (SUPPL., 1):p. S304 Sep. 1999.

Pettersson, F; Colston, KW; Dalgleish, AG: "Differential Control of Cell Growth and Death in Pancreatic Tumour Cells by Retinoids and Vitamin D Analogues," *British Journal of Cancer* 80 (SUPPL. 2):p. 48 Jul. 1999.

Pirianov, G; Colston, KW: "Vitamin D Analogues Suppress IGF-I Signalling and Promote Apoptosis in Human Breast Cancer Cells," *Journal of Endocrinology* 160 (SUPPL.):p. OC3 Mar. 1999.

Lokeshwar, Bal L; Schwartz, Gary G; Selzer, Marie G; Burnstein, Kerry L; Zhuang, Sen-Hong; Block, Norman L; Binderup, Lise: "Inhibition of Prostate Cancer Metastasis in Vivo: A Comparison of 1,25-dihydroxyvitamin D (Calcitriol) and EB1089," *Cancer Epidemiology Biomarkers & Prevention* 8 (3): p. 241-248.

Sundaram, S; Gewirtz, DA: "tk;2EB 1089 Radiosensitizes Breast Tumor Cells," *Proceedings of the American Association for Cancer Research Annual Meeting*, 40p. 144-145 Mar. 1999.

Lee, YY; Seol, JG; Park, WH; Kim, ES; Jung, CW; Binderup, L; Koefler, HP; Kim, BK: "Vitamin $D_3$ Analog, EB1089, Induced Antileukemic Effect of HL-60 Cells Via Activation of Cyclin-Dependent Kinase Inhibitor, p. 21," *Blood* 92 (10 Suppl. 1 Part 1-2):p. 204A Nov. 15, 1998.

Dalhoff, Kim; Astrup, Lone; Bach-Hansen, Jesper; Burcharth, Flemming; Haahr, Hanne Lo; Hamberg, Karin J; Evans, Thomas RJ; Lofts, Fiona; Moller, Susanne; Ranek, Leo; Skovsgaard, Torben; Steward, William P: "Seocalcitol (EB1089), a Vitamin D Analogue, in Hepatocellular Carcinoma," *Hepatology* 28 (4 PART 2):p. 227A Oct. 1998.

Kullenberg, B; Axelson, J: "Analogues of Vitamin $D_3$ Decreases Stimulation of Growth by EGF and TGF-alpha in a Human Pancreatic Cancer Cell Line," *Digestion* 59 (3):p. 220-221 May-Jun. 1998.

Danielsson, Carina; Fehsel, Karin; Carlberg, Carsten: "Antiproliferative Response to Two Human Primary Melanoma Cell Lines to 1,25-dihydroxyvitamin $D_3$ and its Analogues," *Journal of Dermatological Science*, 16 (SUPPL. 1):p. S102 Mar. 1998.

Huynh, Hung: "Regulation of Insulin-Like Growth Factor II (IGF-II) and IGF Binding Protein 3 Autocrine Loop in Human PC-3 Prostate Cancer Cells by 1,25(OH) /2D/3 and its Analog BE1089," *Proceedings of the American Association for Cancer Research Annual Meeting*, 39p. 451 Mar. 1998.

Sundaram, S; Gerwitz, DA: "EB1089 Enhances the Antiproliferative Effects of Radiation in Breast Tumor Cells," *Proceedings of the American Association for Cancer Research Annual Meeting*, 39p. 5 Mar. 1998.

Falzon, Miriam; Zong, Jian: "The Noncalcemic Vitamin D Analogs FB1089 and 22-Oxacalcitriol Suppress Serum-induced parathyroid Hormone-related Peptide Gene Expression in a Lung Cancer Cell Line," *Endocrinology*, 139 (3):p. 1046-1053 Mar. 1998.

Pakkala, S; Sprogel, P; Remes, K; Nousiainen, T; Koivunen, E; Pelliniemi, T-T; Ruutu, T; Elonen, E: EB1089, a Vitamin D Analog in MDS and AML, *Blood* 90 (10 Suppl. 1 Part 1):p. 508A Nov. 15, 1997.

Lee, YY; Park, WH; Seol, JG; Kim, ES; Jung, CW; Binderup, L; Koeffler, HP; Kim, BK: "In Vivo Effect of a Vitamin D/3 Analog, EB1089, on Acute Myelogenous Leukemia," *Blook* 90 (10 Suppl. 1 Part 1):p. 189A Nov. 15, 1997.

Schrader, Magdalena; Kahlen, Jean-Pierre; Carlberg, Carsten: "Functional characterization of a Novel type of 1-Alpha, 25-Hydroxyvitamin D-3 Response Element Identified in the Mouse C-Fos Promoter," *Biochemical and Biophysical Research Communications*, 230 (3):p. 646-651 1997.

Kane, KF; Walker, EA; Langman, MJS; Williams, GR: "Differential Activity of Vitamin Analogues Results From Altered Metabolism," *Journal of Endocrinology*, 151 (SUPPL.) :p. P98 1996.

Xie, SP; James, SY; Colston, KW: "Vitamin D Derivatives Inhibit the Mitogenic Effects of IGF-1 on Human Breast Cancer Cells," *Journal of Endocrinology* 151 (SUPPL.):p. O30 1996.

James, SY; Turner, A; Colston, KW: "Vitamin D Derivatives Potentiate the Induction of Apoptosis in Human Leukaemia Cells by Retinoids," *Journal of Endocrinology* 151 (SUPPL.):p. O29 1996.

Puthier, D; Bataille, R; Barille, S; Mellerin, M-P; Amiot, M: "Potent Cytostatic Effects of EB1089 a New Vitamin D-3 Derivative on Myeloma Cells," *Proceedings of the American Association for Cancer Research Annual Meeting* 37(0):p. 392 1996.

Wu, GF; Sun, LZ; Brattain, MG: "Effects of 1,25(OH)2 Vitamin D3 and its Analogues EB1089 on Regulation of TGF-beta Type II Receptor in Human Breast Cancer MCF-7 Cells," *Proceedings of the American Association for Cancer Research Annual Meeting* 37 (0):p. 226 1996.

Gulliford, T; English, J; Colston, K; Sprogel, P; Coombes, RC: "A Phase 1 Study of EB1089, a Vitamin D Analogue," *Proceedings of the American Association for Cancer Research Annual Meeting*, 37(0):p. 164 1996.

Love-Schimenti, CD; Gibson, DFC; Bikle, DD: "Synergistic Antiproliferative Effects of Vitamin D-3 Analogs and Antiestrogens on ER= and ER– Breast Cancer Cell Lines," *Brease Cancer Research and Treatment*, 37 (SUPPL.):p. 72 1996.

Lee, YY; Kim, ES; Kim, BK; Koeffler, HP: "Effect of a Vitamin D-3 Analog, EB1089, on Peripheral Blood Stem Cell Transplantation in AML," *Blood* 86 (10 SUPPL. 1):p. 143A 1995.

Arbelle, JE; Adams, JS: "Vitamin D-induced CD14 Gene Expression in the Human Myelo-monocytic Cell Line U937: Comparison of 1,25-dihydroxyvitamin D3 with Nonhypercalcemia-causing Analogs," *Journal of Investigative Medicine*, 43 (SUPPL. 2):p. 403A 1995.

Mils, V; Basset-Seguin, N; Moles, JP; Guilhou, JJ: "1,25(OH)2D3 and its Synthetic Derivatives (MC903 and EB1089) Induce a Partial Reversal of Tumoral Phenotype In Vitro," *Journal of Investigative Dermatology* 102(4):p. 642 1994.

De Vos, S; Pakkala, S; Elstner, E; Rude, B; Uskokovic, M; Binderup, L; Koeffler, HP: "Antileukemia Activity and In vivo Calcium—Studies of Several Novel Vitamin D-3 Analogs," *Proceedings of the American Association for Cancer Research Annual Meeting* 35 (0):p. 408 1994.

Lutzky, J; Vujicic, M; Binderup, L; Bhalla, K: "Vitamin D Analogs and Retinoids Exhibit Additive Cytotoxicity to Human Myeloma Cell Lines," *Proceedings of the American Association for Cancer Research Annual Meeting* 35(0):p. 408 1994.

Schilling, T; Albrecht, C; Kohl, B; Ziegler, R; Raue, F: "Vitamin D and its New Analogue EB1089 in the Treatment of the Walker Carcinosarcoma 256, a Rat Model of Hypercalcemia of Malignancy," *Journal of Cancer Research and Clinical Oncology* 120 (SUPPL.):p. R77 1994.

MacKay, AG; James, SY; Ofori-Kuragu, EA; Binderup, L; Colston, KW: "Down-regulation of the Oestrogen Receptor and Induction of Apoptosis in Breast Cancer Cells by EB1089, a Novel Vitamin D Analogue," *Journal of Endocrinology* 139 (SUPPL.):p. P14 1993.

Pakkala, S; Devos, S; Elstner, E; Rude, B; Uskokovic, M; Binderup, L; Koeffler, HP: "Antileukemic Activities and Effects on Serum Calcium of Three Novel Vitamin D-3 Analogs," *Blood* 82 (10 SUPPL. 1):p. 255A 1993.

Hamada, Katsuyuki; Shinomiya, Hiroto: "Novel Vitamin D-3 Analogues and Their Potential for Inhibiting Cancer Cell Growth," *Drugs of the Future* 18 (11):p. 1057-1061 1993.

Posner, GH; Wang, Q; Hah, G; Jae, Kyoo Lee; Crawford, K; Zand, S; Brem, H; Peleg, S; Dolan, P; Kensler, TW: "Conceptually New Sulfone Analogues of the Hormone Lalpha, 25-dihydroxyvitamin Dinf 3: Synthesis and Preliminary Biological Evaluation," *Journal of Medicinal Chemistry* (J. Med. Chem.) (United States) Sep. 9, 1999, 42/18 (3425-3435).

Koshizuka, K; Kubota, T; Said, J; Koike, M; Binderup, L; Uskokovic, M; Koeffler, HP: "Combination Therapy of a Vitamin Dinf 3 Analog and All-trans-retinoic Acid: Effect on Human Breast Cancer in Nude Mice," *Anticancer Research* (Anticancer Res.) (Greece) 1999, 19/1 A (519-524).

Koshizuka, K; Koike, M; Asou, H; Cho, SK; Stephen, T; Rude, RK; Binderup, L; Uskokovic, M; Koeffler, HP: "Combined Effect of Vitamin Dinf 3 Analogs and Paclitaxel on the Growth of MCF-7 Breast Cancer Cells In Vivo," *Breast Cancer Research and Treatment* (Breast Cancer Res. Treat.) (United States) 1999, 53/2 (113-120).

Van Weelden, K; Flanagan, L; Binderup, L; Tenniswood, M; Welsh, J: "Apoptotic Regression of MCF-7 Xenografts in Nude Mice Treated with the Vitamin Dinf 3 Analog, EB1089," *Endocrinology* (United States) 1998, 139/4 (2102-2110).

Jones, G; Strugnell, SA; Deluca, HF: "Current Understanding of the Molecular Actions of Vitamin D," *Physiological Reviews* (Physiol. Rev.) (United States) 1998, 78/4 (1193-1231).

Danielsson, C; Mathiasen, IS; James, SY; Nayeri, S; Bretting, C; Hansen, CM; Colston, KW; Carlberg, C: "Sensitive Induction of Apoptosis in Breast Cancer Cells by a Novel 1,25-dihydroxyvitamin Dinf 3 Analogue Shows Relation to Promoter Selectivity," *Journal of Cellular Biochemistry* (J. Cell. Biochem.) (United States) 1997, 66/4 (552-562).

Naldi, L; "Psoriasis: Latest Advances in Understanding and Nove Therapeutic Approaches. May 12-13, 1997, London, UK," *Expert Opinion on Investigational Drugs* (Expert Opin. Invest. Drugs) (United Kingdom) 1997, 6/7 (895-898).

Schrader, M; Kahlen, JP; Carlberg, C: "Functional Characterization of a Novel Type of Lalpha, 25-dihydroxyvitamin Dinf 3 Response Element Identified in the Mouse c-fos Promoter," *Biochemical and Biophysical Research Communications* (Biochem. Biophys. Res. Commun.) (United States) 1997, 230/3 (646-651).

De Vos, S; Holden, S; Heber, D; Elstner, E; Binderup, L; Uskokovic, M; Rude, B; Chen, DL; Le, J; Cho, SK; Koeffler, HP: "Effects of Potent Vitamin Dinf 3 Analogs on Clonal Proliferation of Human Prostate Cancer Cell Lines," *Prostate* (Prostate) (United States) 1997, 31/2 (77-83).

Lamari, Y; Garel, JM: "Decrease in CGRP and CT Levels Either Contained in or Released by CA-77 C Cells After Combined Treatments with 1,25-dihydroxyvitamin Dinf 3 Analogues and 9-cis Retinoic Acid," *Reproduction Nutrition Development* (Reprod. Nutr. Dev.) (France) 1997 37/1 (3-12).

Akhter, J; Chen, X; Bowrey, P; Bolton, EF; Morris, DL: "Vitamin Dinf 3 Analog, EB1089, Inhibits Growth of Subcutaneous Xenografts of the Human Colon Cancer Cell Line, LoVo, in a Nude Mouse Model," *Diseases of the Colon and Rectum* (Dis.Colon Rectum) (United States) 1997, 40/3 (317-321).

MacKay, AG; Ofori-Kuragu, EA; Lansdown, A; Coombes, RC; Binderup, L; Colston, KW: "Effects of the Synthetic Vitamin D Analogue EB1089 and Tamoxifen on the Growth of Experimental Rat Mammary Tumours," *Endocrine-Related Cancer* (Endocr.-Relat.Cancer) (United Kingdom) 1996 ¾ (327-335).

Musiol, IM; Feldman, D: "1,25-dihydroxyvitamin Dinf 3 Induction of Nerve Growth Factor in L929 Mouse Fibroblasts: Effect of Vitamin D Receptor Regulation and Potency of Vitamin Dinf 3 Analogs," *Endocrinology* (ENDOCRINOLOGY) (United States) 1997, 138/1 (12-18).

James, SY; MacKay, AG; Colston, KW: "Effects of 1,25 Dihydroxyvitamin Dinf 3 and its Analogues on Induction of Apoptosis in Breast Cancer Cells," *Journal of Steroid Biochemistry and Molecular Biology* (J. Steroid Biochem. Mol. Biol.) (United Kingdom) 1996, 58/4 (395-401).

Baudet, C; Chevalier, G; Naveilhan, P; Binderup, L; Brachet, P; Wion, D: "Cytotoxic Effects of Lalpha, 25-dihydroxyvitamin Dinf 3 and Synthetic Vitamin Dinf 3 Analogues on a Glioma Cell Line," *Cancer Letters* (Cancer Lett.) (Ireland) 1996, 100/- (3-10).

Van Den Bemd, GJCM; Pols, Hap; Birkenhager, JC; Kleinekoort, WMC; Van Leeuwen, JPTM: "Differential Effects of 1,25-dihydroxyvitamin Dinf 3-analogs on Osteoblast-like Cells and on In Vitro Bone Resorption," *Journal of Steroid Biochemistry and Molecular Biology* (J. Steroid Biochem. Mol. Biol.) (United Kingdom) 1995, 55/3-4 (336-346).

Roy, S; Martel, J; Tenenhouse, HS: "Comparative Effects of 1,25-dihydroxyvitamin Dinf 3 and EB1089 on Mouse Renal and Intestinal 25-hydroxyvitamin Dinf 3-24-hydroxylase," *Journal of Bone and Mineral Research* (J. Bone Miner. Res.) (United State) 1995, 10/12 (1951-1959).

Kissmeyer, AM; Mathiasen, IS; Latini, S; Binderup, L: "Pharmacokinetic Studies of Vitamin D Analogues: Relationship to Vitamin D Binding Protein (DBP)," *Endocrine* (ENDOCRINE) (United Kingdom) 1995, ¾ (263-266).

Wijngaarden, TVV; Birkenhager, JC; Kleinekoort, WMC; Van Den Bemd, GJCM; Pols, Hap; Van Leeuwen, JPTM: "Antiestrogens Inhibit in vitro Bone Resorption Stimulated by 1,25-dihydroxyvitamin Dinf 3 and the Vitamin Dinf 3 Analogs EB1089 and KH1060," *Endocrinology* (Endocrinology)(United States) 1995, 136/2 (812-815).

Pakkala, S; De Vos, S; Elstner, E; Rude, RK; Uskokovic, M; Binderup, L; Koeffler, HP: "Vitamin Dinf 3 Analogs: Effect on Leukemic Clonal Growth and Differentiation, and on Serum Calcium Levels," *Leukemia Research* (Leuk.Res.) (United Kingdom) 1995, 19/1 (65/72).

Carlberg, C; Mathiasen, LIS; Saurat, J; Binderup, L: "The 1,25-dihydroxyvitamin Dinf 3 (VD) Analogues MC903, EB1089 and KH1060 Activate the VD Receptior: Homodimers Show Higher Ligand Sensitivity Than Heterodimers with Retinoid X Receptors," *Journal of Steroid Biochemistry and Molecular Biology* (J. Steroid Biochem. Mol. Biol.) (United Kingdom) 1994, 51/3-4 (137-142).

Hamada, K; Shinomiya, H: "Novel Vitamin Dinf 3 Analogs and Their Potential for Inhibiting Cancer Cell Growth," *Drugs of the Future* (Drugs Future) (Spain) 1993, 18/11 (1057-1061).

Koli, K; Keski-Oja: "Vitamin Dinf 3 and Calcipotriol Decrease Extracellular Plasminogen Activator Activity in Cultured Keratinocytes," *Journal of Investigative Dermatology* (J. Invest. Dermatol.) (United States) 1993, 101/5 (706-712).

Binderup, L: "Vitamin D Analogues: New Regulators of Cancer Cell Growth and Differentiation," *Bioorganic and Medicinal Chemistry Letters* (Bioorg. Med. Chem. Lett.) (United Kingdom) 1993, 3/9 (1891-1896).

Haq, M; Kremer, R; Goltzman, D; Rabbani, SA: "A Vitamin-D Analog (EB1089) Inhibits parathyroid-Hormone Related Peptide Production and Prevents the Development of Malignancy-Associated Hypercalcemia Invivo," *Journal of Clinical Investigation*, 1993, V91, N6 (Jun), p. 2416-2422.

Kabanos, TA; White, AJP; Williams, DJ; Woollins, JD: "Synthesis and X-Ray Structures of Bis(3,5-di-tert-butylcatecholato)(phenanthroline)vanadium (iv) and its Vanadium (v)," *Journal of the chemical Society*—Series Chemical Communications (J. Chem. Soc. Ser. Chem. Commun.) (United Kingdom) 1992, -1/ (17-18).

\* cited by examiner vitamin D₃

1α,25-(OH)₂-D₃

1α,25-(OH)₂-16-ene-23-yne-D₃ (analog V)

1α,25-dihydroxy-22,24-diene-24,26,27-trihomovitamin D (EB1089)

METHOD AND PRODUCT FOR TREATING CANCER IN PETS

FIELD OF THE INVENTION

The present invention relates to a method for treating disease in pets, and more particularly for treating cancer in dogs and cats through addition of vitamin D or an analog of vitamin D to pet food, and to pet food containing vitamin D or a vitamin D analog.

BACKGROUND OF THE INVENTION

Pets play an important role in many peoples lives, and consequently many pet owners will go to considerable lengths to treat their pets for major illnesses, such as cancer. Cancer is one of the major forms of mortality in pets such as cats and dogs, and therefore the pet owners desire ways of treating this disease in their pets to increase their longevity. Such treatments ideally would be not only economical, but also practical for owners rather than veterinarians to administer to the pet.

Present methods of treating cancer in pets focus primarily on surgical resection of solid tumors. Surgery is expensive, and moreover, is not suitable treatment for many cancers. Among these are leukemias and lymphomas, where surgery obviously is not an option, but this class includes highly disseminated malignancies as well as ones with poorly defined margins or those arising in inoperable locations.

It would therefore be desirable to have a way of treating cancer in dogs and other pets that could be administered routinely by pet owners and that would not be resisted by the pet. Ideally, such treatment could be administered with the pet's food.

SUMMARY OF THE INVENTION

The present invention meets these needs by providing a pet food that contains vitamin D or a derivative of vitamin D, hereinafter referred to generically as "vitamin D analogs", where the term "vitamin D analogs" specifically includes $1,25\text{-}(OH)_2D_3$, analog V, and EB 1089, the structures of which appear in FIG. 1. The present invention further provides for a method of treating cancer in a pet, such as a cat or dog, through feeding the animal a pet food containing at least one vitamin D analog.

BRIEF DESCRIPTIONS OF THE DRAWINGS

DETAILED DESCRIPTION OF THE INVENTION

Vitamin D displays a wide range of physiological activities, including stimulation of the immune system, mobilization of calcium from the skeletal system, and cell differentiation, that have suggested its use for treating hypertension, diabetes mellitus, autoimmune diseases, AIDS, host versus graft reactions, and even strengthening egg shells.

Of particular relevance to the present invention, $1,25(OH)_2D_3$ also stimulates differentiation of cells and inhibits excessive cell proliferation such as occurs in cancer. U.S. Pat. No. 4,391,802 issued to Suda et al. discloses that 1α-hydroxyvitamin D compounds induce differentiation of leukemia cells to nonmalignant macrophages (monocytes), and are useful in the treatment of leukemia in humans. In another example, Skowronski et al. reported anti-proliferative and differentiating actions of vitamin $D_3$ analogs on cell lines derived from human prostate cancers (Skowronski et al 1995).

In four thyroid anaplastic carcinoma cell lines, $1,25\text{-}(OH)_2D_3$ caused diphasic cell growth in three of the four cell lines, while the vitamin D analog 22-oxacalcitriol showed dose-dependent inhibition of cell growth in all four of the cell lines. (Suzuki et al 1999) $1,25\text{-}(OH)_2D_3$ has anti-proliferative activity in some human and rat liver cancer cell lines, but other cell lines resist its action. (Pourgholami et al 2000).

$1,25\text{-}(OH)_2D_3$ also inhibits cell growth and promotes differentiation in a dose-dependent manner in a human prostate cancer cell line ((Moffatt et al 1999). $1,25\text{-}(OH)_2D_3$ has significant antitumor effects in the murine squamous cell carcinoma (SCC) tumor model in vitro and in vivo (Hershberger et al 1999).

In addition to the antiproliferative effect of $1,25(OH)_2D_3$ on tumor cells, $1,25(OH)_2D_3$ and its analogs stimulates differentiation in squamous cell carcinoma (McElwain et al 1995), (Kornfehl et al 1996), (Yu et al 1995), (Hershberger et al 1999).

In canine-derived cell lines, treatment of four osteosarcoma cell lines with $1,25(OH)_2D_3$ increases alkaline phosphatase activity in one cell line, osteocalcin production in two lines and type I collagen production in three lines (Nozaki et al 1999). In a canine squamous carcinoma cell line (SCC 2/88) $1,25\text{-}(OH)_2D_3$ stimulates production of parathyroid hormone-related protein (PTHrP), a major causative factor in humoral hypercalcemia of malignancy (Merryman et al 1993).

The applicants have found that $1,25(OH)_2D_3$, 22,24-diene-24,26a,27a-trihomo-1α,25-dihydroxyvitamin $D_3$ (EB 1089) and 1,25-dihydroxy-16-ene-23-yne-vitamin D (analog V) inhibit cell proliferation in vitro in the canine-derived SCC 2/88 cell line at a concentration of $10^{-7}$ M, while EB 1089 inhibits cell growth significantly at concentrations of $10^{-7}$M and $10^{-9}$ M (on three-day treatment).

Figure 1:
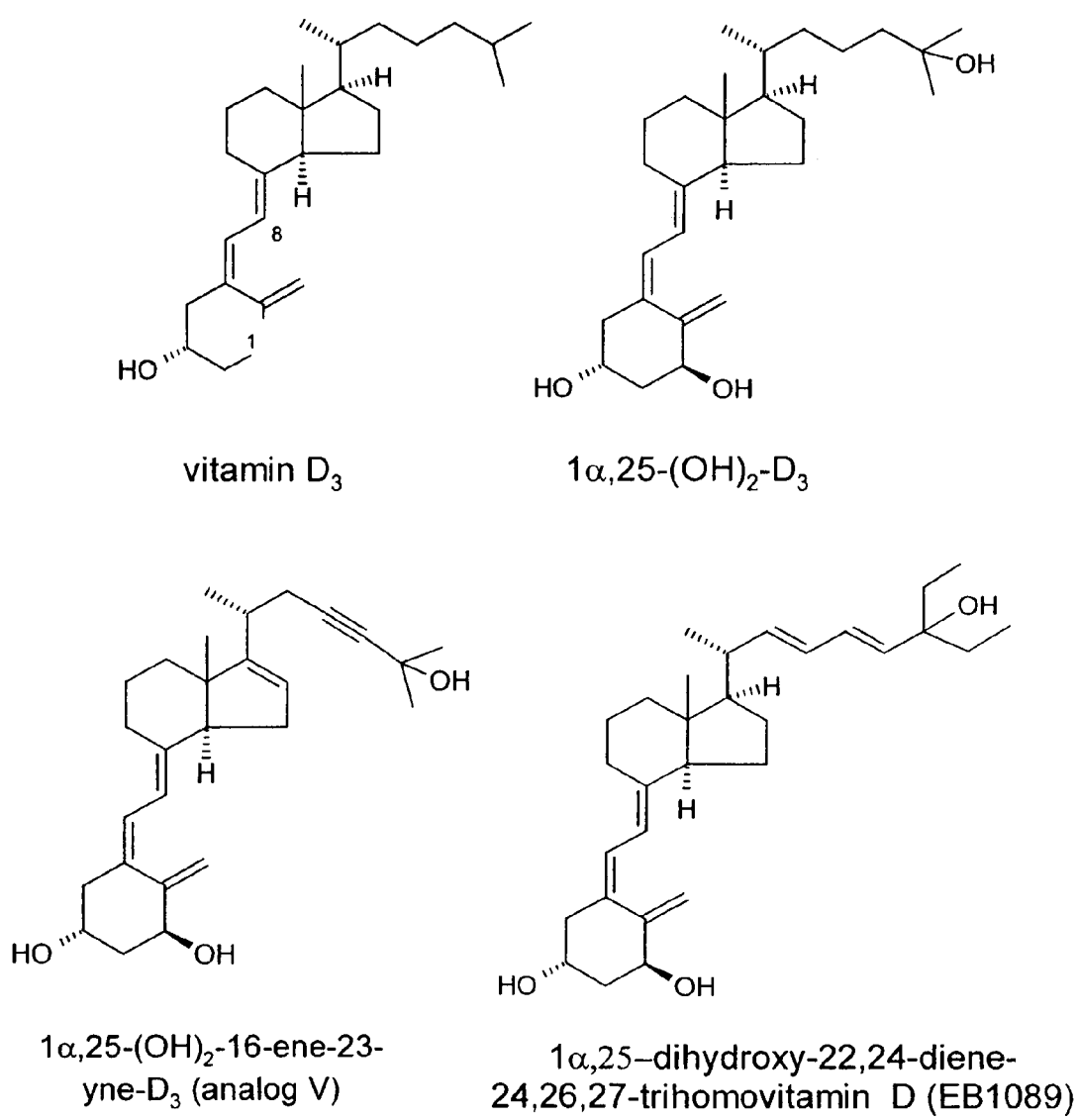
FIG. 1 shows the chemical structures of vitamin $D_3$, $1,25\text{-}(OH)_2D_3$, EB 1089, and analog V.

FIG. 1 shows the chemical structures of vitamin $D_3$, 1,25-$(OH)_2D_3$, 1a,25-$(OH)_2$-16-ene-23-yne-vitamin D (analog V), and 1a,25-dihydroxy-22,24-diene24,26,27-trihomo vitamin D (EB 1089).

Figure 2:
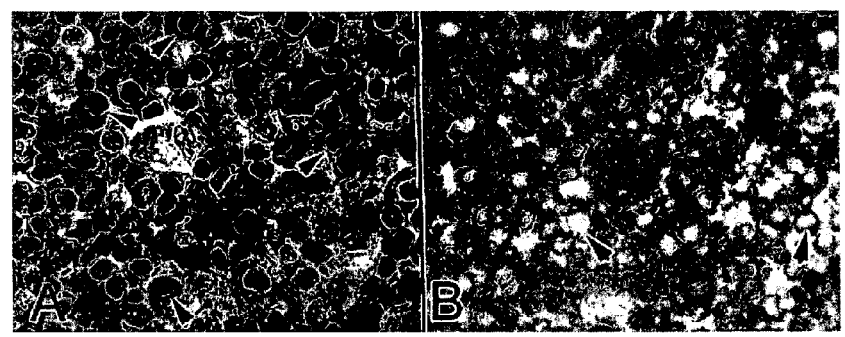
FIG. 2 is a microphotograph (×300) of SCC 2/88 cells immunohistochemically stained with monoclonal anti-vitamin D receptor-antibody, after treatment with $1,25\ (OH)D_3$ (left) or with vehicle (right)

FIG. 2 is a microphotograph (×300) of SCC 2/88 cells immunohistochemically stained with vitamin D receptor-antibody (left) and treated with non-specific antiserum. The left hand side of FIG. 2 shows cellular expression of the vitamin D receptor, showing positive labeling in all nuclei of tumor cells (arrowheads). The positive peroxidase reaction in nuclei of carcinoma cells establishes that these cells derived from canine squamous cell carcinoma have receptors for vitamin D. The control section (right) after reaction with non-specific antiserum in place of a specific primary antibody shows the absence of reaction product in the cell nuclei (arrowheads).

Figure 3:
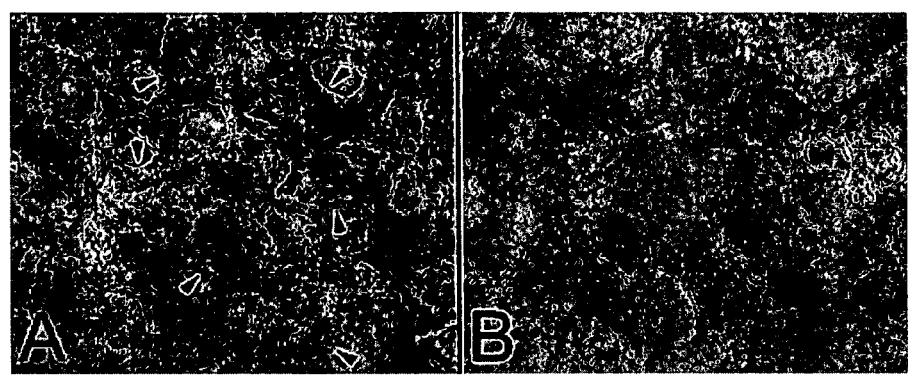
FIG. 3 is a microphotograph (×300) of SCC 2/88 cells immunohistochemically stained with (left) rabbit anti-human parathyroid hormone-related protein (PTHrP), and (right) with non-specific antiserum.

FIG. 3 is a microphotograph (×300) of SCC 2/88 cells immunohistochemically stained with (left) rabbit anti-human parathyroid hormone-related protein (PTHrP), showing positive reaction for PTHrP in cell cytoplasm (arrowheads), and (right) SCC 2/88 cells after reaction with non-specific antiserum in place of a specific primary antibody, showing the absence of reaction product in the cell cytoplasm.

Figure 4:
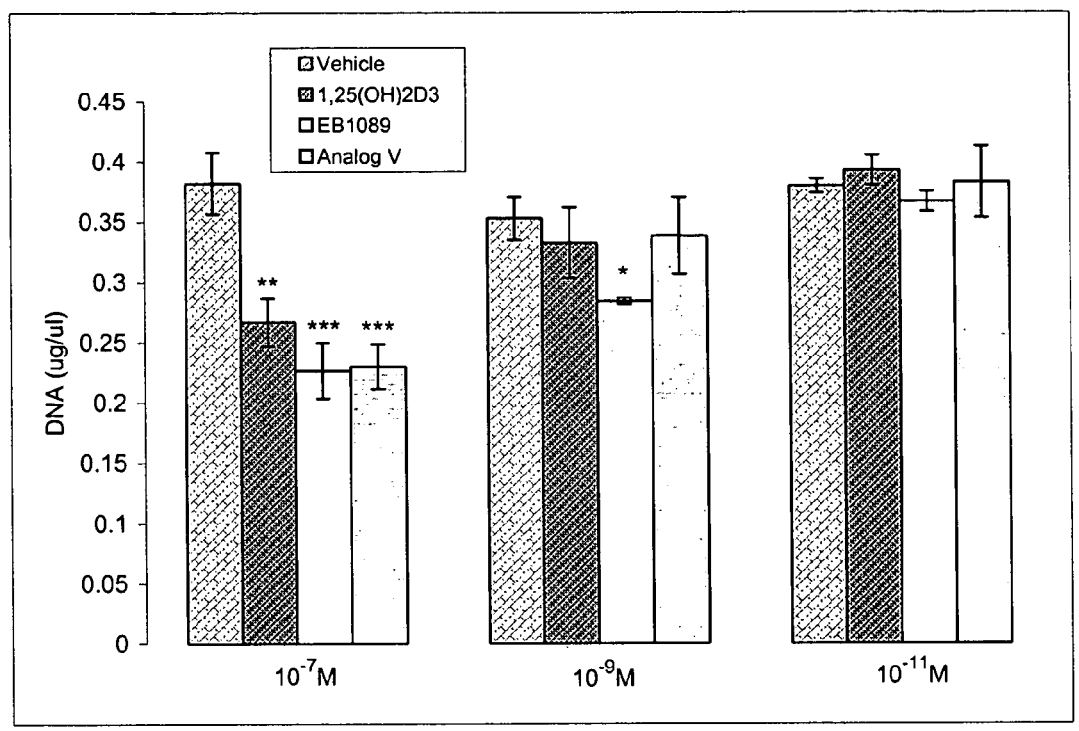
FIG. 4 is a histogram showing the growth of SCC 2/88 cells after addition of different concentrations of $1,25(OH)_2D_3$ and its analogs to the culture medium.

FIG. 4 is a histogram showing the effect of different concentrations of $1,25(OH)_2D_3$ and its analogs on the growth of SCC 2/88 cells. Addition of a vitamin D analog to the culture medium inhibited cell growth in a dose-dependent manner. Growth of SCC 2/88 cells significantly reduced the concentration of DNA (μg/μl) at $10^{-7}$ M of $1,25(OH)_2D_3$ ($p<0.01$), EB 1089 ($p<0.001$), and analog V ($p<0.001$) and at $10^{-9}$ M of EB 1089 ($p<0.05$).

Figure 5:
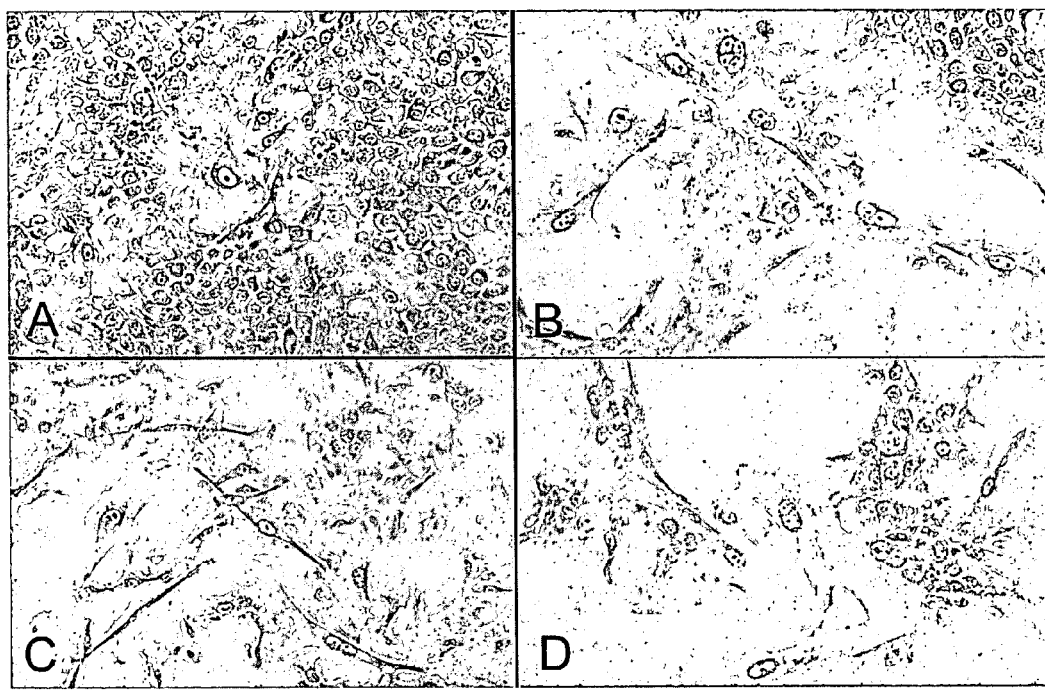
FIG. 5 is a phase contrast microphotograph (×100) showing the morphology of SCC 2/88 cells grown in 6-well plates and treated with (A) vehicle, (B) $1,25\text{-}(OH)_2D_3$; (C) EB 1089; and (D) analog V.
Figure 6:
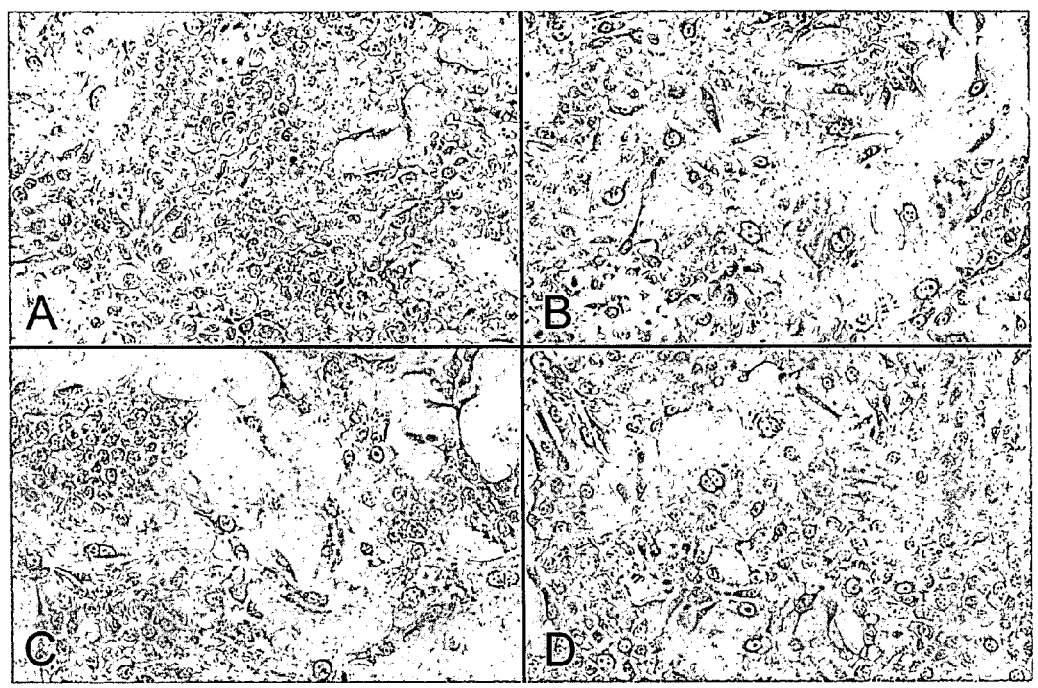
FIG. 6 is a phase contrast microphotograph (×100) showing the morphology of SCC 2/88 cells grown in 6-well plates on day 3 in the absence of a vitamin D analog.

FIG. 5 and FIG. 6 are phase contrast microphotographs (×100) of SCC 2/88 cells on day 3 in the presence and absence (respectively) of $1,25(OH)_2D_3$ and its analogs at concentrations of $10^{-7}$ M and $10^{-9}$ M, showing that no significant differences in cell morphology were apparent.

Figure 7:
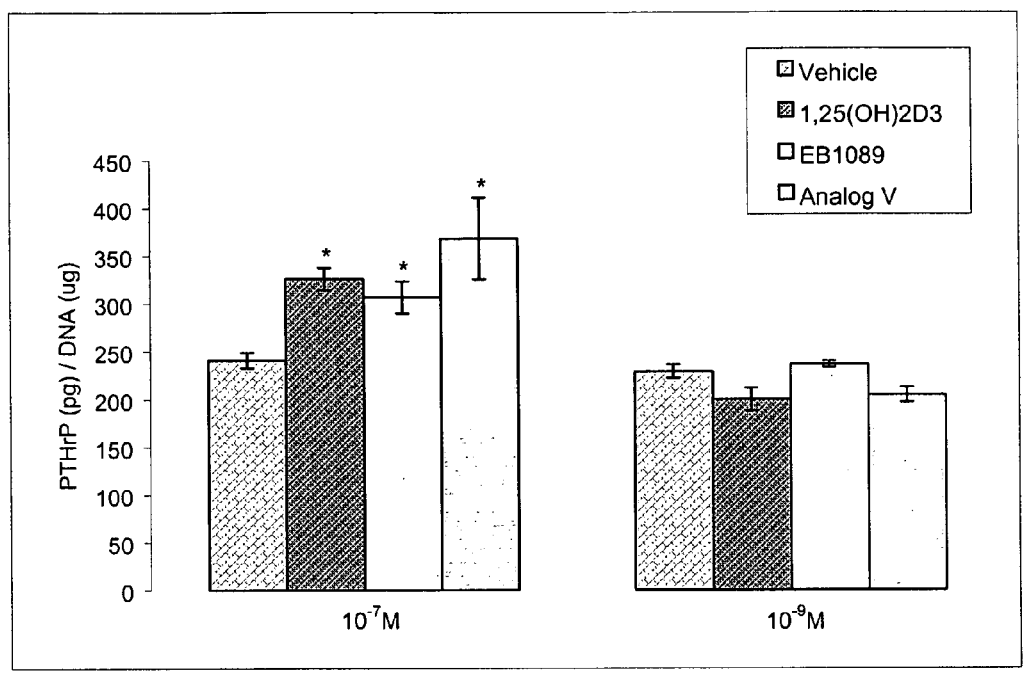
FIG. 7 is a histogram showing PTHrP production as measured by release of PTHrP (pg) per DNA (μg) in SCC 2/88 cells treated with vitamin D analogs compared to the vehicle-treated control.

FIG. 7 is a histogram showing PTHrP production as measured by release of PTHrP (pg) per DNA (μg). Levels of PTHrP (pg)/DNA (μg) by day 3 significantly increased in all three substrate-treated groups ($p<0.05$) treated with $10^{-7}$ M vitamin D analog compared to the vehicle-treated control. At $10^{-9}$ M concentration no vitamin D analog produced a significant difference in PTHrP production, as measured by PTHrP (pg)/DNA (μg).

SCC 2/88 cells constitutively produce PTHrP, which is associated with humoral hypercalcemia of malignancy, at a level that depends on the duration of culture and confluence of cells (Werkmeister et al 1993). $1,25(OH)_2D_3$, EB 1089, and analog V promote PTHrP production in the canine SCC 2/88 cell line (Merryman et al 1993). On the contrary, in human squamous cell lines, $1,25(OH)_2D_3$ inhibits PTHrP production, suppresses PTHrP gene transcription, and prevents development of the humoral hypercalcemia of malignancy syndrome (Yu et al 1995), (Falzon 1997), (Abe at al 1998,El Abdaimi et al 1999). The effects of vitamin D analogs on cells of different species are, therefore, unpredictable.

$1,25(OH)_2D_3$ was used to investigate the expression of PTHrP mRNA. Transforming growth factors (TGF-β, TGF-α) and interleukin-1 (IL-1) are coproduced with PTHrP in humoral hypercalcemia of malignancy. Particularly, TGF-β copurified with PTHrP from many human and animal cancer-associated with humoral hypercalcemia of malignancy (Merryman et al 1994), (Insogna et al 1987). Thus, we also compared the effects of TGF-β and anti-TGF-β on PTHrP mRNA expression with the biologically active vitamin D, $1,25(OH)_2D_3$.

In SCC 2/88 cells, TGF-β increases PTHrP production via up-regulating in an autocrine manner, which aggravates the severity of the hypercalcemia (Merryman et al 1993), (Merryman et al 1994). Correspondingly, levels of PTHrP mRNA in SCC 2/88 cells treated with TGF-β increase 2- to 20-fold after 24 hr compared with the vehicle-treated control, in contrast to cells treated with anti-TGF-β. Levels of PTHrP mRNA in cells treated with $1,25(OH)_2D_3$ and TGF-β, however, increased less than in cells treated with TGF-β alone. Cells treated with $1,25(OH)_2D_3$ and TGF-β show 1- to 3-fold higher PTHrP mRNA levels than cells treated with $1,25(OH)_2D_3$ alone. Levels of TGF-β mRNA between $1,25(OH)_2D_3$-treated group and vehicle-treated control did not differ. $1,25(OH)_2D_3$ and TGF-β may therefore upregulate PTHrP production and mRNA expression in SCC 2/88 cells in part due to increased gene transcription. This was most evident at 6 to 12 hr post-treatment. Furthermore, $1,25(OH)_2D_3$ probably affects TGF-β by reducing PTHrP mRNA expression, but not directly decreasing TGF-β mRNA expression.

Figure 8:
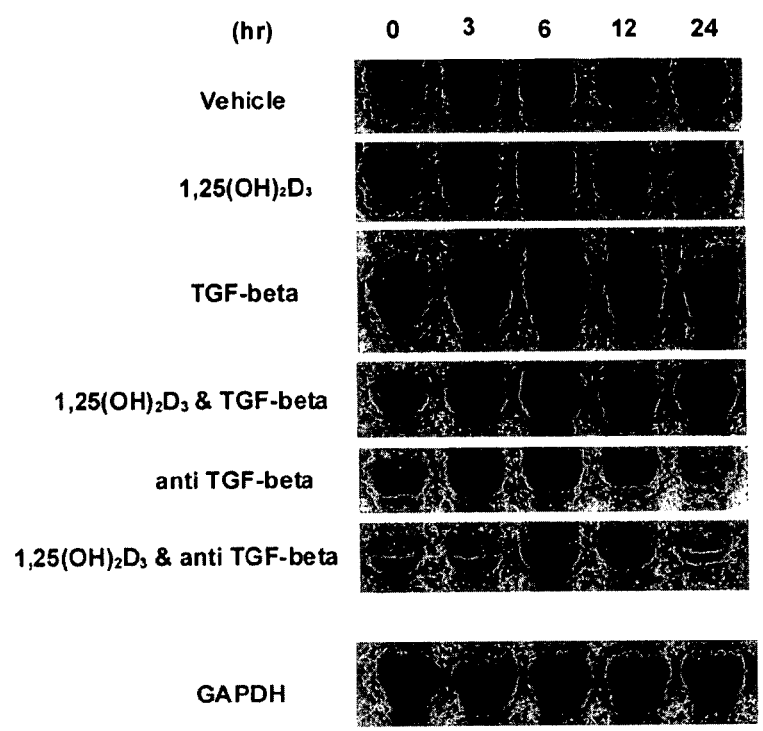
FIG. 8 shows a Northern blot analysis of PTHrP mRNA expression in SCC 2/88 cells treated with vehicle, $1,25(OH)_2D_3$, TGF-β, $1,25(OH)_2D_3$ and TGF-β, anti-TGF-β, $1,25(OH)_2D_3$ and anti-TGF-β.

FIG. 8 shows a Northern blot analysis of PTHrP mRNA expression in SCC 2/88 cells treated with vehicle, $1,25(OH)_2D_3$, TGF-β, $1,25(OH)_2D_3$ and TGF-β, anti-TGF-β, $1,25(OH)_2D_3$ and anti-TGF-β. PTHrP mRNA was detectable at all time points (0, 3, 6, 12 and 24 hrs.). All of the lanes were standardized with the glyceraldehyde 3-phosphate dehydrogenase mRNA loading control.

Figure 9:
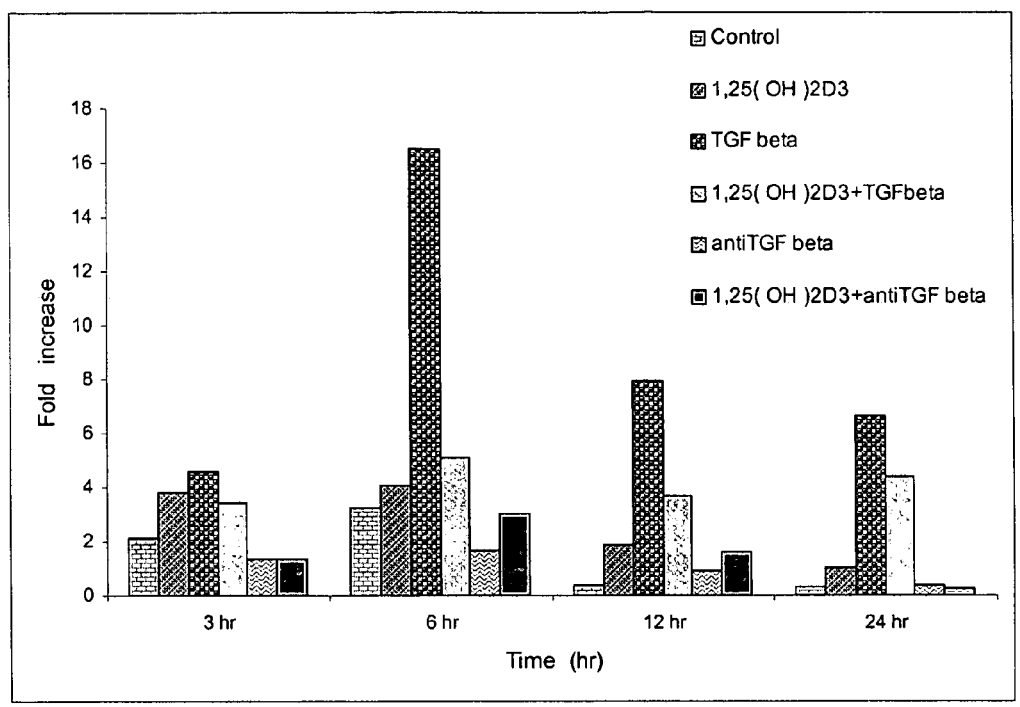
FIG. 9 is a histogram showing PTHrP mRNA expression in the $10^{-7}$ M $1,25(OH)_2D_3$-treated cells at 24 hr and in the $10^{-7}$ M $1,25(OH)_2D_3$ and TGF-β (1.5 ng/mL)-treated cells at 3 and 6 hr compared to vehicle-treated control.

FIG. 9 is a histogram showing approximately 1- to 2-fold increases in PTHrP mRNA in the $10^{-7}$ M $1,25(OH)_2D_3$-treated cells at 24 hr and in the $10^{-7}$ M $1,25(OH)_2D_3$ and TGF-β (1.5 ng/mL)-treated cells at 3 and 6 hr compared to vehicle-treated control. Levels of PTHrP mRNA in cells treated with TGF-β (1.5 ng/mL) showed a steeper increase of 5- to 20-fold at 6, 12, and 24 hr compared with the vehicle-treated control. Similarly, the levels of PTHrP mRNA in $10^{-7}$ M $1,25(OH)_2D_3$ and TGF-β-treated cells (1.5 ng/mL) displayed a 10- to 15-fold greater increase at 12 and 24 hr respectively compared with the vehicle-treated control. Conversely, cells treated with anti-TGF-β (5 μg/mL) or with a combination of $1,25(OH)_2D_3$ ($10^{-7}$ M) and anti-TGF-β (5 μg/mL) showed modest decreases in PTHrP mRNA expression at 24 hr compared to the vehicle-treated control.

Figure 10:
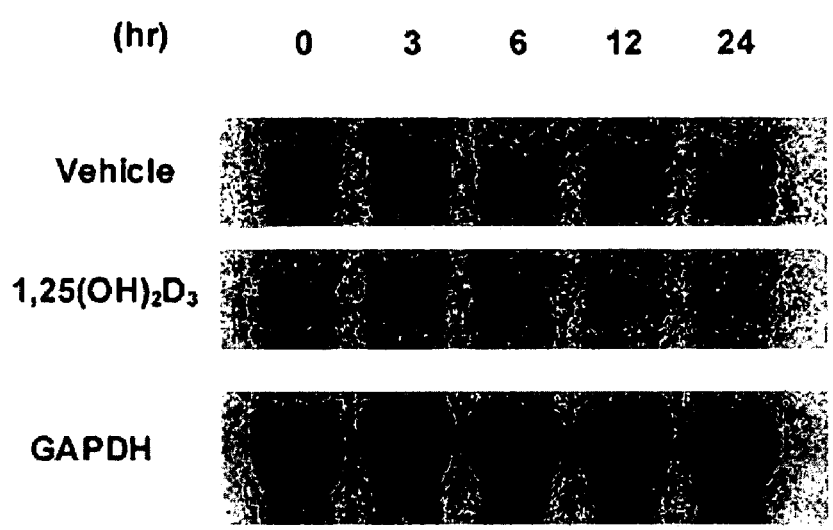
FIG. 10 is a time course Northern blot analysis of TGF-β mRNA expression in SCC 2/88 cells treated with vehicle or $1,25(OH)_2D_3$.

FIG. 10 is a Northern blot analysis of TGF-β mRNA expression in SCC 2/88 cells treated with vehicle and $1,25(OH)_2D_3$. TGF-β mRNA was detectable at all time points (0, 3, 6, 12 and 24 hrs.), and expression in $10^{-7}$ M $1,25(OH)_2D_3$-treated cells did not differ significantly from that in the vehicle-treated control cells.

Figure 11:
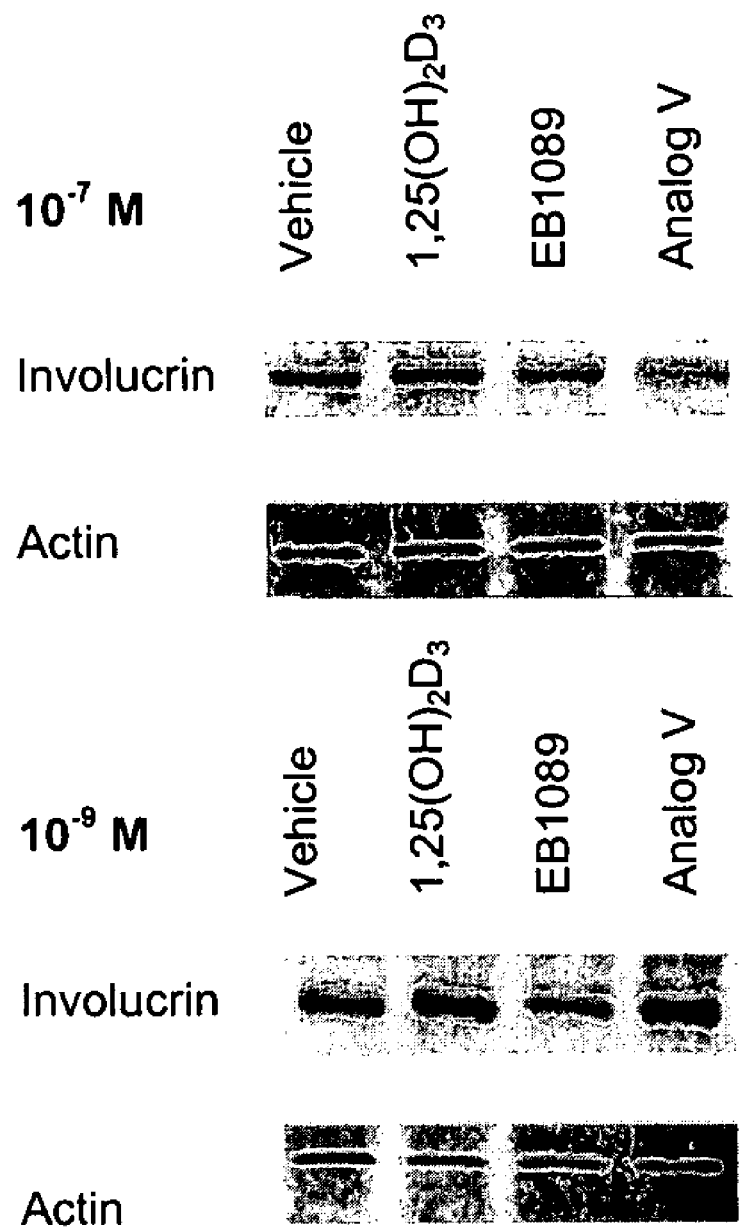
FIG. 11 shows a SDS-PAGE and Western blot analysis for involucrin in SCC 2/88 cells treated with EB 1089 ($10^{-7}$ M) and analog V ($10^{-7}$ M and $10^{-9}$ M).

FIG. 11 shows a SDS-PAGE and Western blot analysis for involucrin in SCC 2/88 cells treated with EB 1089 ($10^{-7}$ M) and analog V ($10^{-7}$ M and $10^{-9}$ M). Cells treated with either with EB 1089 or with analog V (at $10^{-7}$ M in each case) gave bands on the nitrocellulose sheet (molecular weight ca. 66 kDa) that bound a mouse monoclonal antibody against involucrin. Anti-involucrin reactive bands for both EB 1089 ($10^{-7}$ M) and analog V ($10^{-7}$ M) were more weakly defined than that of the vehicle-treated control. Anti-involucrin reactive bands of cells treated with $10^{-9}$ M analog V were more intense than those of the other treated groups.

Vitamin D analogs inhibit cell growth, as measured by involucrin determinations. Involucrin, a precursor of epidermal cornified envelope, is a marker for squamous epithelium and of terminal differentiation such that decreases in involucrin expression indicate increased cell differentiation. Treatment of post-confluent SCC 2/88 cells with $1,25(OH)_2D_3$, EB 1089, and analog V (at $10^{-7}$ M) and $1,25(OH)_2D_3$ and EB 1089 (at $10^{-9}$ M) for up to seven days diminished involucrin expression.

Treatment of cells with $10^{-7}$ M EB 1089 and analog V yielded weak or substantially absent anti-involucrin reactive bands, compared to cells treated with vehicle alone. Treatment of cells with $10^{-9}$ M EB 1089 also showed diminished levels of involucrin by Western blot analysis. Furthermore, treatment with EB 1089 or analog V (each at $10^{-7}$ M) significantly diminished cell growth ($p<0.001$); treatment with EB 1089 ($10^{-9}$ M) reduced cell growth at a lower confidence level ($p<0.05$). In contrast, treatment with analog V ($10^{-9}$ M) gave a stronger anti-involucrin reactive band, with no significant inhibition of cell growth.

The applicants have therefore shown that vitamin D analogs inhibit proliferation and promote differentiation in canine cancer cells. Parenteral administration of vitamin D analogs to pets would necessitate the involvement of a veterinarian, which would substantially increase the expense. The applicants have found, however, that enteral administration of vitamin D analogs is also effective for cancer therapy in dogs, and that incorporating vitamin D analogs into dog food is an effective and practical way of routinely administering vitamin D analogs to a pet suffering from cancer. In practice, the therapeutic efficacy against cancer of a pet food containing vitamin D analog is evaluated by methods well-known to those skilled in the relevant art. For example Valierus et al. detail methodology used for evaluating a variety of anti-cancer therapies, the entire disclosure of which is hereby incorporated by reference (Valerius et al 1997).

The vitamin D analog incorporated into dog food can be processed in accordance with conventional methods to produce pharmaceutical agents for administration to patients, e.g., in admixtures with conventional excipients such as pharmaceutically acceptable organic or inorganic carrier substances suitable for oral administration that do not deleteriously react with the active compounds. Suitable pharmaceutically acceptable carriers include but are not limited to water, salt (buffer) solutions, alcohols, gum arabic, mineral and vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, and polyvinyl pyrrolidone. The pharmaceutical preparations can be mixed, if desired, with auxiliary agents, e.g., lubricants, preservatives, stabilizers, wetting agents, emulsifiers, salts for influencing osmotic pressure, buffers, coloring, flavoring and/or aromatic active compounds. The dosage forms may also contain adjuvants, such as preserving or stabilizing adjuvants. They may also contain other therapeutically valuable substances or may contain more than one of the compounds specified herein and in the claims in admixture.

In general, the daily dosage of the compounds according to this invention generally is about 0.025 to about 500 nmol/kg of body weight of the patient, and preferably about 0.025 to about 100 nmol/kg. In a more preferred embodiment, the daily dosage is about 0.025 to about 10 nmol/kg of body weight of the patient, and in a most preferred embodiment the daily dosage is from about 0.025 to about 1 nmol/kg of body weight of the patient.

In addition, those skilled in the art will also appreciate that such dosages may be encapsulated in time release, e.g., sustained, delayed or directed release delivery systems such as a liposome delivery system, polysaccharides exhibiting a slow release mechanism, salistic or other polymer implants or microspheres, as well as those where the active ingredient is suitably protected with one or more differentially degradable coatings, e.g., by microencapsulation, enteric coating, multiple coatings, etc., and such means effect continual dosing of compositions contained therein. For example, an enteric coating is suitably one which is resistant to disintegration in gastric juice.

It will be appreciated that the actual preferred amounts of active analog in a specific case will vary according to the specific compound being used, the particular compositions formulated, the mode of application, and the particular sites being treated. Dosages can be determined using conventional considerations, e.g., by customary comparison of the differential activities of the subject compounds and of a known agent, e.g., by means of an appropriate conventional pharmacological protocol.

The specific doses for each particular patient depend on a wide variety of factors, for example, on the efficacy of the specific compound employed, on the age, body weight, general state of health, sex of patient, on the diet, on the timing and mode of administration, on the rate of excretion, and on medicaments used in combination and the severity of the particular disorder to which the therapy is applied.

The dosage forms may also contain adjuvants as well as other therapeutically valuable substances or may contain more than one of the compounds specified herein in admixture. Thus, a further aspect within the scope of the present invention is administration of effective dosages of the compounds of the present invention in conjunction with administration of other hormones or other agents that have been shown to have efficacy in the treatment and present of the diseases and disorders described herein.

For example, compounds of the present invention are suitably co-administered with agents known to ameliorate bone diseases or disorders. Such bone agents may include conjugated estrogens or their equivalents, antiestrogens, calcitonin, bisphosphonates, calcium supplements, calcium receptor agonists, cobalamin, pertussis toxin, boron, dehydroepiandrosterone (DHEA) and other bone growth factors such as transforming growth factor beta, activin or bone morphogenic protein.

Also provided herein are compounds of the present invention that are co-administered with known cytotoxic agents. Such agents include estramustine phosphate, prednimustine, cisplatin, 5-fluoro-uracil, melphalan, hydroxyurea, mitomycin, idarubicin, methotrexate, adriamycin, daunomycin, cyclophosphamide, doxorubicin (hydroxydaunorubicin), vincristine (oncovin) and pregnisone. It is anticipated that a 1α-hydroxyvitamin D of the present invention used in combination with various anticancer drugs can give rise to a significantly enhanced cytotoxic effect on cancerous cells, thus providing an increased therapeutic effect. Specifically, as a significantly increased growth-inhibitory effect is obtained with the above-disclosed combinations utilizing lower concentrations of the anticancer drugs compared to the treatment regimens in which the drugs are used alone, there is the potential to provide therapy wherein adverse side effects associated with the anticancer drugs are considerably reduced than normally observed with the anticancer drugs used alone in larger doses. Possible dose ranges of these co-administered second anticancer agents are about 0.1 μg to 1 μg/kg/day.

The compounds in accordance with the present invention are also suitably co-administered with known antiinflammatory agents. Such agents include both steroidal (e.g., corticosteroids) and nonsteroidal antiinflammatory agents (e.g., salicylates, naproxen). It is anticipated that a compound of the present invention used in combination with these various anti-inflammatory drugs can give rise to a significantly enhanced anti-inflammatory activity, thus providing an increased therapeutic effect.

For treatment purposes, the active compounds of this invention can be formulated as solutions in innocuous solvents, or as emulsions, suspensions or dispersions in suitable innocuous solvents or carriers, or as pills, tablets or capsules, containing solid carriers according to conventional methods known in the art. Any such formulations may also contain other pharmaceutically-acceptable and non-toxic excipients such as stabilizers, anti-oxidants, binders, coloring agents or emulsifying or taste-modifying agents.

The present invention is further explained by the following examples, which should not be construed by way of limiting the scope of the present invention.

EXAMPLES

Materials and Methods

Vitamin D and its analogs. A 1 mM stock solution of $1,25(OH)_2D_3$ and each of its analogs in absolute ethanol was prepared and protected from light. Maximum concentration of ethanol in the culture ($\leq 0.1\%$) did not influence cell growth or differentiation. Stock solutions of each compound were made in ethanol and Williams' E media (W ME) to concentrations of $10^{-7}$ M, $10^{-9}$ M, and 10–11 M just prior to culture.

Cell culture. SCC 2/88 cells were grown in W ME supplemented with 10% fetal bovine serum, 50 μg/mL of gentamicin, 10 ng/mL of epidermal growth factor (Gibco BRL, Grand Island, N.Y.), 0.1 nM Cholera toxin (Calbiochem, La Jolla, Calif.), and 2 mM L-glutamine (Gibco BRL, Grand Island, N.Y.) at 37° C., 5% $CO_2$, humidified atmosphere. Cells were seeded at a density of $10^5$ cells/well in 6-well culture plates (Becton Dickinson, Franklin Lakes, N.J.) and grown for 24 hours before starting experiments (day 0). After a 24-hour incubation at 37° C., medium containing vehicle (ethanol), $1,25(OH)_2D_3$, or its analogs (EB 1089 and analog V) was added at $10^{-7}$ M, $10^{-9}$ M, and $10^{-11}$ M and was changed every day for up to 3 days. Each experiment was run in triplicate. Media were collected every 24 hours for 3 days and stored at −70° C. until assayed for PTHrP content by immunoradiometric assay. At the end of day 3, cells were retrieved from the 6-well culture plates by use of 250 μl GITC (4 M guanidine isothiocyanate, 0.5% sarcocyl, 25 mM sodium citrate) per well and stored at −70° C. until assayed for cell proliferation by fluorescence DNA concentration analysis.

For RNA isolation, SCC 2/88 cells ($2 \times 10^6$ cells/mL) were seeded in 90-mm tissue culture dishes (Becton Dickinson, Franklin Lakes, N.J.) and grown up to 70% confluence in W ME media containing 10% FBS. Cells were incubated in the media without FBS for 24 hours before the time of treatment. Cells were treated with $10^{-7}$ M $1,25(OH)_2D_3$, 1.5 ng/mL of TGFβ, and 5 μg/mL of anti-TGFβ for 0, 3, 6, 12 hours. Cells were washed (phosphate buffered saline), trypsinized, and stored at −70° C. until assayed by northern blot analysis.

Fluorescence DNA Concentration Analysis.

DNA content of cell lysates was determined by DNA fluorometry through use of a fluorescent plate reader and analyzer (IDEXX Laboratories Inc., Westbrook, Me.) and Hoechst 33258 dye (Hoefer Scientific Instruments, San Francisco, Calif.). Calf thymus DNA (100 μg/mL) served as a calibration control.

Total RNA Isolation and Northern Blot Analysis.

Total RNA was isolated by use of a Purescript® RNA isolation kit (Gentra systems, Minneapolis, Minn.) according to the procedures recommended by the manufacturer. Equal amounts of each RNA sample (20 μg loaded in each lane) were separated on a 1.2% agarose-formaldehyde gel, and transferred to a nylon membrane (Poll Biosupport, East Hills, N.Y.). Northern blotting was conducted using standard procedures (Sambrook et al. 1989). Blot was hybridized with a $^{32}P$-labeled cDNA probe (NEN life science products, Inc. Boston, Mass.). The nylon membrane was washed twice with a solution of 2× standard saline citrate buffer and 0.1%(w/v) sodium dodecyl sulfate at room temperature for 15 minutes, then washed once with a solution of 0.1× standard saline citrate buffer and 0.1%(w/v) sodium dodecyl sulfate for 30 minutes at 60° C. for a high-stringency wash. Subsequently, the membrane was exposed through use of a phosphoimager screen. After exposure, the membrane was stripped and hybridized with a glyceraldehyde 3-phosphate dehydrogenase cDNA probe to normalize for RNA loading.

PTHrP Immunoradiometric Assay.

Medium (200 μl) collected from cells treated with vehicle, $1,25(OH)_2D_3$, or its analogs (at concentrations of $10^{-7}$ M and $10^{-9}$ M) on days 0, 1, 2, and 3 in triplicate was assayed for PTHrP content. PTHrP was measured using immunoradiometric assay kit (DiaSorin Corp., Stillwater, Minn.) with human recombinant PTHrP 1–84 for standards and controls. Immunoradiometric assay was performed by binding of anti-PTHrP 1–40 antibody to polystyrene beads and labeling of the anti-PTHrP 57–80 antibody with 125I. Samples were incubated with the antibodies, and the polystyrene beads were then washed to remove any unbound-labeled antibody. The radioactivity remaining from the bound-labeled antibody was measured with a gamma-radiation counter. PTHrP content was quantified through use of a GraphPad Prism™ program (GraphPad software Inc., San Diego, Calif.).

Cell pellet procedure for immunohistochemical staining. SCC 2/88 cells were grown to approximately $8-9 \times 10^6$ cells on 10-mm tissue culture dishes. Cells were trypsinized and centrifuged at 3000 G, 4° C. for 10 minutes. Supernatant was suctioned off to leave the cell pellet. Dissolved agarose was added to hold cells together. Immediately, the pellet was fixed in 2-methylbutane in liquid nitrogen for 20 seconds, and then was placed in the fixative (0.5% glutaraldehyde in absolute ethanol) overnight at −70° C. The pellet was dehydrated in absolute ethanol for an hour and in acetone twice for 30 minutes, respectively. The pellet was embedded and cut at 5 μm for immunohistochemical evaluation.

Immunohistochemistry.

Staining for vitamin D receptor distribution was performed by incubating respectively with 5% normal goat serum in phosphate buffered saline (pH 7.4) for 30 minutes, primary antibody—rat monoclonal antibody against the vitamin D receptor (Chemicon International Inc., Temecula, Calif.) 1:50 at 4° C. overnight, secondary antibody—goat anti-rat IgG (Chemicon International Inc., Temecula, Calif.) 1:20 in phosphate buffered saline for 30 minutes, rat peroxidase-anti-peroxidase (PAP) (Chemicon International Inc., Temecula, Calif.) 1:100 in 1% normal goat serum in phosphate buffered saline for 30 minutes, and 0.05% diaminobenzidine and 0.01% hydrogen peroxide in 0.05 M Tris buffer for 5 minutes. Slides were washed between each step with phosphate buffered saline, then dehydrated, mounted with aqua-Mount and visualized by light microscopy.

For PTHrP distribution the staining was done by blocking with 3% $H_2O_2$ for 20 minutes and incubating respectively with 2% normal horse serum in phosphate buffered saline for 20 minutes, primary antibody—rabbit anti-human PTHrP (Oncogene research products, Cambridge, Mass.) 1:100 in primary antibody diluent at 4° C. overnight, secondary antibody-biotinylated goat anti-rabbit IgG (Calbiochem, La Jolla, Calif.)) 1:500 in phosphate buffered saline for an hour, avidin-biotin complex (Pierce, Rockford, Ill.) for 30 minutes, and diaminobenzidine for 5 minutes. Slides were washed between each step with phosphate buffered saline and distilled water, then dehydrated, mounted with aqua-Mount and visualized by light microscopy.

Cell differentiation. Involucrin was extracted from cultured SCC 2/88 cells grown in 175 cm2 culture flasks (Becton Dickinson, Franklin Lakes, N.J.) for one week. Post confluent cells were treated with either vehicle, $1,25(OH)_2 D_3$, EB 1089, or analog V at concentrations $10^{-7}$ M and $10^{-9}$ M for up to 7 days. Cells were washed and released from the culture flask with phosphate buffered saline containing 20 mM EDTA. Cells were disrupted with a Branson sonifier (Branson Ultrasonic Corporation, Danbury, Conn.) at a setting of 6 for 3×30 seconds and centrifuged at 100,000 G for 30 minutes at 10° C. The supernatant (cytosol) was made 10% in glycerol and 62.5 mM in Tris-HCl (pH 6.8) and heated for 10 minutes at 100° C. The denatured proteins were removed by centrifugation at 15,000 G for 15 minutes. Involucrin in the supernatant was collected stored at –70° C. until Western blot analysis was performed.

Western Blot Analysis.

Extracted proteins (20 μg) were separated by electrophoresis through 7.5 % sodium dodecyl sulfate (SDS)-polyacrylamide gel, and transferred to nitrocellulose membrane with use of a semi-dry transferred technique (Bio-Rad laboratories, Hercules, Calif.). The membrane was then blocked in blocking solution (10% dry milk, 0.05% Tween 20 in phosphate buffered saline) overnight at 4° C. The preblocked membrane was incubated in mouse monoclonal antibody against involucrin (Research Diagnotics Inc., Flanders, N.J.) 1:500 for an hour and extensively washed in PBS (pH 7.4) containing 0.05% Tween 20. The blot was then incubated in goat anti-mouse IgG (horseradish peroxidase) (Bio-Rad laboratories, Hercules, Calif.) 1:500 for an hour. After further washing in phosphate buffered saline containing 0.05% Tween 20, the blot was developed for 1 minute in the LumiGLO Chemiluminescent substrate (Kirkegaard and Perry laboratories, Gaithersburg, Md.), and then exposed to x-ray film for 1–5 seconds. After exposure, the membrane was stripped and incubated with mouse monoclonal anti-β-actin (Sigma, Saint Louis, Mo.) to normalize for protein loading. AlphaImager™ Alpha Innotech Corporation, San Leandro) measured the density of involucrin bands.

Statistical Analysis.

Numerical data from PTHrP production and DNA concentration studies were analyzed by one-way analysis of variance (ANOVA), and Turkey's multiple comparisons test. Data from PTHrP (pg) per DNA (μg) studies were analyzed by t-test and ANOVA. The level of significance were established at p<0.05, p<0.01, or p<0.001 using Instat program (Graph PAD software Inc., San Diego, Calif.). The results were expressed as the mean±standard error of the mean (SE M) (n=3). All treatment groups were tested in triplicate.

REFERENCES

Abe M, Akeno N, Ohida S, Horiuchi N (1998), Inhibitory effects of 1,25-dihydroxyvitamin D3 and 9-cis-retinoic acid on parathyroid hormone-related protein expression by oral cancer cells (HSC-3), *J.Endocrinol.* 156: 349–357

El Abdaimi K, Papavasiliou V, Rabbani S A, Rhim J S, Goltzman D, Kremer R (1999), Reversal of hypercalcemia with the vitamin D analogue EB 1089 in a human model of squamous cancer, *Cancer Res.* 59: 3325–3328

Falzon M (1997), The noncalcemic vitamin D analogues EB1089 and 22-oxacalcitriol interact with the vitamin D receptor and suppress parathyroid hormone-related peptide gene expression, *Mol. Cell Endocrinol.* 127: 99–108

Hershberger P A, Modzelewski R A, Shurin Z R, Rueger R M, Trump D L, Johnson C S (1999), 1,25-Dihydroxycholecalciferol (1,25-D3) inhibits the growth of squamous cell carcinoma and down-modulates p21(Waf1/Cip1) in vitro and in vivo, *Cancer Res.* 59: 2644–2649

Insogna K L, Weir E C, Wu T L, Stewart A F, Broadus A E, Burtis W J, Centrella M (1987), Co-purification of transforming growth factor beta-like activity with PTH-like and bone-resorbing activities from a tumor associated with humoral hypercalcemia of malignancy, *Endocrinology* 120: 2183–2185

Kornfehl J, Formanek M, Temmel A, Knerer B, Willheim M (1996), Antiproliferative effects of the biologically active metabolite of vitamin D3 (1,25 $[OH]_2 D_3$) on head and neck squamous cell carcinoma cell lines, *Eur. Arch. Otorhinolaryngol.* 253: 341–344

McElwain M C, Dettelbach M A, Modzelewski R A, Russell D M, Uskokovic M R, Smith D C, Trump D L, Johnson C S (1995), Antiproliferative effects in vitro and in vivo of 1,25-dihydroxyvitamin $D_3$ and a vitamin $D_3$ analog in a squamous cell carcinoma model system., *Mol. Cell. Diff* 3: 31–50

Merryman J I, Capen C C, McCauley L K, Werkmeister J R, Suter M M, Rosol T J (1993), Regulation of parathyroid hormone-related protein production by a squamous carcinoma cell line in vitro, *Lab Invest* 69: 347–354

Merryman J I, DeWille J W, Werkmeister J R, Capen C C, Rosol T J (1994), Effects of transforming growth factor-beta on parathyroid hormone-related protein production and ribonucleic acid expression by a squamous carcinoma cell line in vitro, *Endocrinology* 134: 2424–2430

Moffatt K A, Johannes W U, Miller G J (1999), 1 Alpha,25dihydroxyvitamin D3 and platinum drugs act synergistically to inhibit the growth of prostate cancer cell lines, *Clin. Cancer Res.* 5: 695–703

Nozaki K, Kadosawa T, Nishimura R, Mochizuki M, Takahashi K, Sasaki N (1999), 1,25-Dihydroxyvitamin D3, recombinant human transforming growth factor-beta 1, and recombinant human bone morphogenetic protein-2 induce in vitro differentiation of canine osteosarcoma cells, *J. Vet. Med. Sci.* 61: 649–656

Pourgholami M H, Akhter J, Lu Y, Morris D L (2000), In vitro and in vivo inhibition of liver cancer cells by 1,25-dihydroxyvitamin D3, *Cancer Lett.* 151: 97–102

Sambrook et al. (1989), *Molecular Cloning: A Laboratory Manual*, Cold Spring Harbor, N.Y.

Skowronski R J, Peehl D M, Feldman D (1995), Actions of vitamin $D_3$, analogs on human prostate cancer cell lines: comparison with 1,25-dihydroxyvitamin $D_3$, *Endocrinology* 136: 20–26

Suzuki S, Takenoshita S, Furukawa H, Tsuchiya A (1999), Antineoplastic activity of 1,25(OH)2D3 and its analogue 22-oxacalcitriol against human anaplastic thyroid carcinoma cell lines in vitro, *Int. J. Mol. Med.* 4: 611–614

Valerius K D, Ogilvie G K, Mallinckrodt C H, Getzy D M (1997), Doxorubicin alone or in combination with asparaginase, followed by cyclophosphamide, vincristine, and prednisone for treatment of multicentric lymphoma in dogs: 121 cases (1987–1995), *J. Am. Vet. Med. Assoc.* 210: 512–516

Werkmeister J R, Merryman J I, McCauley L K, Horton J E, Capen C C, Rosol T J (1993), Parathyroid hormone-related protein production by normal human keratinocytes in vitro, *Exp. Cell Res.* 208: 68–74

Yu J, Papavasiliou V, Rhim J, Goltzman D, Kremer R (1995), Vitamin D analogs: new therapeutic agents for the treatment of squamous cancer and its associated hypercalcemia, *Anticancer Drugs* 6: 101–108

What is claimed is:

1. A method of treating SCC 2/88, a canine squamous carcinoma cell line, for cancer, comprising the step of feeding a dog a dog food comprising a proteinaceous component, a farinaceous component, and a therapeutic agent comprising a vitamin D analog selected from the group consisting of $1\alpha,25\text{-(OH)}_2D_3$, $1\alpha,25\text{-(OH)}_2\text{-16-ene-23-yne-}D_3$ and $1\alpha,25\text{-(OH)}_2\text{-22,24-diene-24,26,27-trihomo-}D_3$ and stereoisomers thereof.

2. The method of claim 1, wherein the vitamin D analog is $1\alpha,25\text{-(OH)}_2D_3$ and stereoisomers thereof.

3. The method of claim 1, wherein the vitamin D analog is $1\alpha,25\text{-(OH)}_2\text{-16-ene-23-yne-}D_3$ and stereoisomers thereof.

4. The method of claim 1, wherein the vitamin D analog is $1\alpha,25\text{-(OH)}_2\text{-22,24-diene-24,26,27-trihomo-}D_3$ and stereoisomers thereof.

5. The method of claim 1, wherein the vitamin D analog is administered in combination with a bone agent, a cytotoxic agent, an immuno response regulating agent, an antinflammatory agent or combinations thereof.

6. The method of claim 1, wherein the dog is fed from about 0.025 to about 500 nmol/kg of body weight of the patient per day of the vitamin D analog.

7. The method of claim 1, wherein the dog is fed from about 0.025 to about 100 nmol/kg of body weight of the patient per day of the vitamin D analog.

8. The method of claim 1, wherein the dog is fed from about 0.025 to about 10 nmol/kg of body weight of the patient per day of the vitamin D analog.

9. The method of claim 1, wherein the dog is fed from about 0.025 to about 1.0 nmol/kg of body weight of the patient per day of the vitamin D analog.

10. The method of claim 1, wherein the dog is fed a therapeutically efficacious dosage of a vitamin D analog.

11. The method of claim 1 wherein the Vitamin D analog is administered in combination with a bone agent comprising at least one of conjugated estrogens, conjugated estrogen equivalents, anti-estrogens, calcitonin, bisphosphonates, calcium supplements, calcium receptor agonists, cobalamin, pertussis toxin, boron, dehydroepiandrosterone, activin and bone morphogenic protein.

12. The method of claim 1 wherein the Vitamin D analog is administered in combination with a cytotoxic agent comprising at least one of estramustine phosphate, prednimustine, cisplatin, 5-fluoro-uracil, melphalan, hydroxyurea, mitomycin, idarubicin, methotrexate, adriamycin, daunomycin, cyclophosphamide, doxorubicin, vincristine and prednisone.

13. The method of claim 1 wherein the Vitamin D analog is administered in combination with an anti-inflammatory agent comprising at least one of a steroidal anti-inflammatory agent and a non-steroidal anti-inflammatory agent.

14. The method of claim 13 wherein the steroidal anti-inflammatory agent includes corticosteroids.

15. The method of claim 13 wherein the non-steroidal anti-inflammatory agent includes at least one of salicylates and naproxen.

16. The method of claim 1 wherein feeding the dog a therapeutic agent comprising a vitamin D analog comprises producing a pharmaceutical agent from admixture which includes at least one of a pharmaceutically acceptable organic carrier substance and a pharmaceutically acceptable inorganic carrier substance.

17. The method of claim 16 wherein the pharmaceutically acceptable organic carrier substance and the pharmaceutically acceptable inorganic carrier substance include at least one of water, salt and buffer solutions, alcohols, gum arabic, mineral and vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, and polyvinyl pyrrolidone.

18. The method of claim 16 further comprising mixing the pharmaceutical agent with an auxiliary agent, the auxiliary agent including one or more of lubricants, preservatives, stabilizers, wetting agents, emulsifiers, salts for influencing osmotic pressure, buffers, coloring, flavoring and/or aromatic active compounds.

19. A method of providing a therapeutic agent to a pet, wherein the agent comprises a vitamin D analog selected from the group consisting of $1\alpha,25\text{-(OH)}_2D_3$, $1\alpha,25\text{-(OH)}_2\text{-16-ene-23-yne-}D_3$, and $1\alpha,25\text{-(OH)}_2\text{-22,24-diene-24,26,27-trihomo-}D_3$ and stereoisomers thereof, said method comprising providing a pet food including a proteinaceous component, a farinaceous component, and the agent, and feeding the pet food to a pet.

20. The method of claim 19 wherein the vitamin D analog is administered in combination with at least one of a bone agent, a cytotoxic agent, an immuno response regulating agent, and an anti-inflammatory agent.

21. The method of claim 19 wherein the dog is fed from about 0.025 to about 500 nmol/kg of body weight of the dog per day of the vitamin D analog.

22. The method of claim 19 wherein the dog is fed from about 0.025 to about 100 nmol/kg of body weight of the dog per day of the vitamin D analog.

23. The method of claim 19 wherein the dog is fed from about 0.025 to about 10 nmol/kg of body weight of the dog per day of the vitamin D analog.

24. The method of claim 19 wherein the dog is fed from about 0.025 to about 1.0 nmol/kg of body weight of the dog per day of the vitamin D analog.

25. The method of claim 19 wherein the dog is fed a therapeutically efficacious dosage of the vitamin D analog.

26. A method of administering a pharmaceutical agent to a pet, wherein the agent comprises a vitamin D analog selected from the group consisting of $1\alpha,25\text{-(OH)}_2D_3$, $1\alpha,25\text{-(OH)}_2\text{-16-ene-23-yne-}D_3$, and $1\alpha,25\text{-(OH)}_2\text{-22,24-}$ diene-24,26,27-trihomo-$D_3$ and stereoisomers thereof, said method comprising providing a pet food including a proteinaceous component, a farinaceous component, and the agent, and feeding the pet food to a pet.

27. The method of claim 26 wherein feeding the pet food to a pet comprises producing a pharmaceutical agent from an admixture which includes at least one of a pharmaceutically acceptable organic carrier substance and a pharmaceutically acceptable inorganic carrier substance.

28. The method of claim 27 wherein the pharmaceutically acceptable organic carrier substance and the pharmaceutically acceptable inorganic carrier substance include at least one of water, salt (buffer) solutions, alcohols, gum arabic, mineral and vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, and polyvinyl pyrrolidone.

29. The method of claim 27 further comprising mixing the pharmaceutical agent with an auxiliary agent that includes one or more of lubricants, preservatives, stabilizers, wetting agents, emulsifiers, salts for influencing osmotic pressure, buffers, coloring, flavoring and/or aromatic active compounds.

30. The method of claim 26 wherein the dog is fed from about 0.025 to about 500 nmol/kg of body weight of the dog per day of the vitamin D analog.

31. The method of claim 26 wherein the dog is fed a therapeutically efficacious dosage of a vitamin D analog.

* * * * *